(12) United States Patent
Waldmann

(10) Patent No.: US 7,094,404 B1
(45) Date of Patent: Aug. 22, 2006

(54) METHOD FOR TREATING MALIGNANCY AND AUTOIMMUNE DISORDERS IN HUMANS USING TAC ANTIBODIES

(75) Inventor: Thomas A. Waldmann, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/478,748

(22) Filed: Jun. 7, 1995

Related U.S. Application Data

(63) Continuation-in-part of application No. 07/879,056, filed on Apr. 30, 1992, now abandoned, which is a continuation of application No. 07/767,538, filed on Sep. 27, 1991, now abandoned, which is a continuation of application No. 07/085,707, filed on Aug. 17, 1987, now abandoned.

(51) Int. Cl.
   *A61K 39/395* (2006.01)

(52) U.S. Cl. ............... 424/154.1; 424/130.1; 424/133.1; 424/138.1; 424/141.1; 424/143.1; 424/144.1; 424/153.1; 424/155.1; 424/156.1; 424/173.1; 424/174.1; 424/178.1; 424/181.1; 424/183.1; 424/1.49

(58) Field of Classification Search ............... 424/130.1, 424/133.1, 193.1, 154.1, 173.1, 178.1, 1.49, 424/138.1, 141.1, 144.1, 153.1, 155.1, 156.1, 424/174.1, 181.1, 183.1
See application file for complete search history.

(56) References Cited

PUBLICATIONS

Rubin et al. Ann. Int. Med. 113: 619–627 (1990).*
Waldmann et al. Blood 82 : 1701–1712, 1993.*
Waldmann et al. Blood 86: 4063–4075 (1995).*
Vriesendorp et al. Int. J. Radiation Oncology 22:37–45 (1991).*
Kozak et al. PNAS 83:474–478 (1986).*
Diamanstein et al. Immunol. Rev. 92:5–27(1986).*
Order et al. Int. J. Radiat. Oncol. Biol. Phys 12: 277–281 (1986).*
Wessels et al. Med Phys 11: 638–645(1984).*
Waldmann Important Advances in Oncology 1994 Devita et al. (ED) J. B. Lippincott Co. Philadelphia.*
Waldmann Leukemia 7 (Suppl. 2) S151–S156 (1993).*
Hakimi et al. J. Immunol. 147: 1352–1359(1991).*
Kreitman et al. Bioconjugate Chem. 4: 112–120(1993).*
Parenteau et al. Transplantation 54: 963–968 (1992).*
The Merck Manual of Diagnosis and Therapy 16th Edition Beretow et al., Eds., Merck Research Laboratories Rahway NJ 1992 pp. 2610–2617.*
T.A. Waldmann, "Lymphokine Receptors: A Target For Immunotherapy of Lymphomas," *Annals of Oncology*, vol. 5, pp. 13–17, 1994.
Paul S. Brown, Jr. et al., "Anti–Tac–H, a Humanized Antibody to the Interleukin 2 Receptor, Prolongs Primate Cardiac Allograft Survival," *Proc. Natl. Acad. Sc.*, vol. 88, pp. 2663–2667, Apr. 1991.
Robert J. Kreitman, et al., "The Recombinant Immunotoxin Anti–Tac (Fv)–Pseudomonas Exotoxin 40 is Cytotoxic Toward Peripheral Blood Malignant Cells From Patients with Adult T–Cells Leukemia," *Proc. Natl. Acad. Sci*, vol. 87, pp. 8291–8295, Nov. 1990.
R.P. Junghans, et al., " Anti–Tac–H, a Humanized Antibody to the Interleukin 2 Receptor with New Features for Immunotherapy in Malignant and Immune Disorders," *Cancer Research*, vol. 50, pp. 1495–1502, Mar. 1, 1990.

* cited by examiner

*Primary Examiner*—Phillip Gambel
(74) *Attorney, Agent, or Firm*—Leydig, Voit & Mayer, LTD

(57) ABSTRACT

The present invention relates to a method for treating conditions associated with elevated levels of Tac-positive cells, including malignancy and autoimmune disorders and for preventing allograft rejection. $^{90}$Y-Conjugated anti-Tac or Ricin A conjugated anti-Tac and optionally unconjugated anti-Tac antibodies are employed to treat the above conditions. Clinical therapies have been designed to treat immune diseases and lymphomas in patients using conjugated anti-Tac antibodies.

1 Claim, 9 Drawing Sheets

FIG. 5
Before Treatment
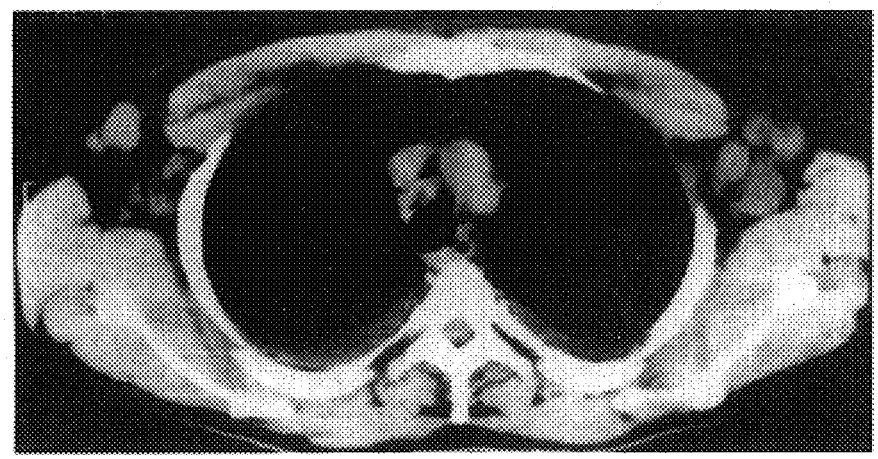
After 2 Doses $^{90}$-Y-$\alpha$-Tac
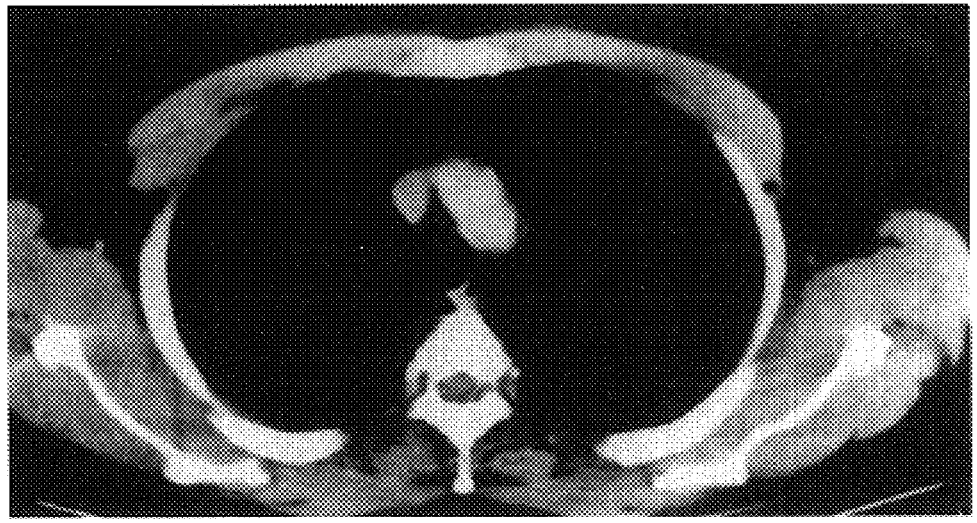

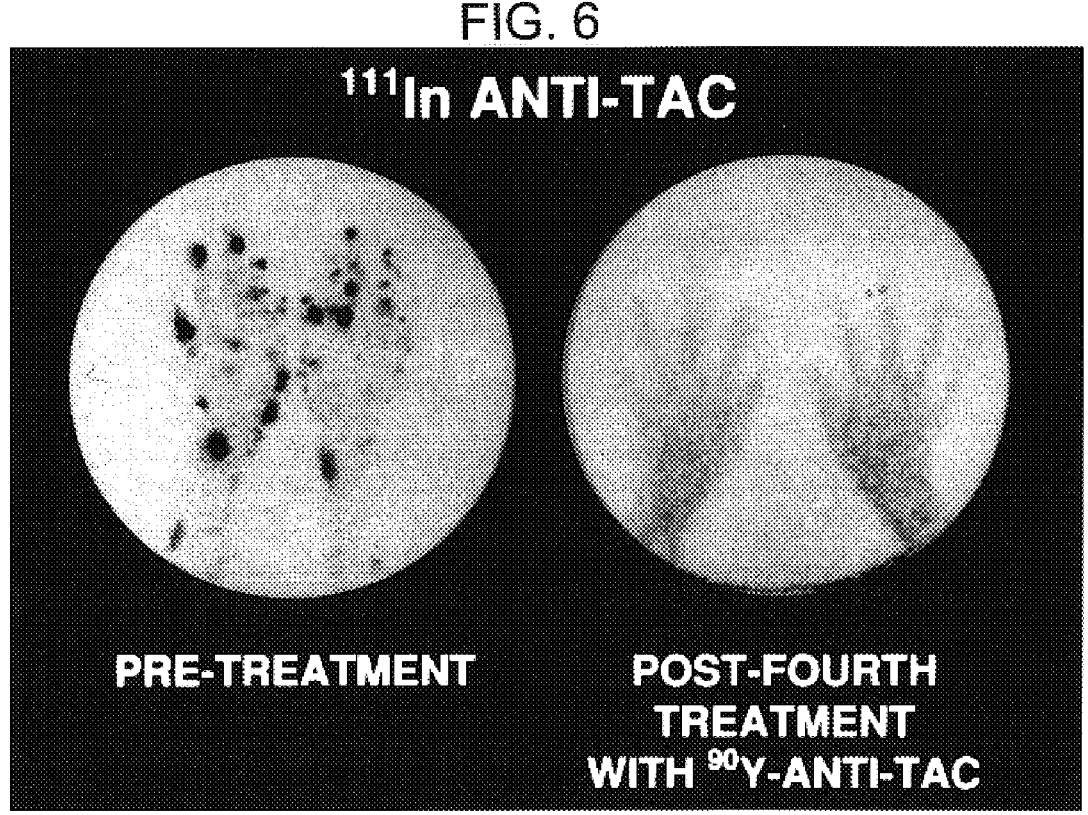

METHOD FOR TREATING MALIGNANCY AND AUTOIMMUNE DISORDERS IN HUMANS USING TAC ANTIBODIES

The instant application is a continuation-in-part of application Ser. No. 07/879,056, filed Apr. 30, 1992, now abandoned which is a continuation of application Ser. No. 07/767,538, filed Sep. 27, 1991, now abandoned which is a continuation of application Ser. No. 07/085,707, filed Aug. 17, 1987, now abandoned.

BACKGROUND OF THE INVENTION

1. Technical Field

The present invention is related to a method for treating malignancy and autoimmune disorders and for preventing allograft rejection. More particularly, the present invention is directed to treating any human condition or disorder related to the expression of Tac antigen or involving abnormal IL-2- receptor expression, by reacting Tac antigen or IL-2 receptor expressing cells with anti-Tac antibody or a preparation thereof.

2. State of the Art

The normal resting cells of the body, including T cells, do not express IL-2 receptors and thus do not react with a monoclonal antibody anti-Tac that recognizes the human IL-2 receptor. However, in certain conditions, such as in leukemic T cells of patients infected with human T-cell lymphotrophic virus I (HTLV-I-associated Adult T Cell Leukemia), large numbers of IL-2 receptors are constitutively expressed.

The Tac antigen (also referred to herein as "IL-2Rα") is also expressed in other malignant conditions including the malignant B lymphocytes of Hairy cell leukemia, follicular lymphoma and the Reed-Sternberg cells of Hodgkin's disease. Furthermore, activated T cells expressing the Tac antigen also appear to play a pathogenic role in certain forms of autoimmune disorders, such as type I diabetes and a subset of patients with aplastic anemia. In addition, when cells responding to foreign histocompatibility antigens become activated, they express the Tac antigen and participate in allograft rejection such as in patients receiving vascularized organ allografts and in graft-versus-host disease in patients receiving marrow allografts. Thus, there are a number of clinical circumstances where the expression of Tac-antigen is involved. Clearly, therefore, the elimination of Tac-positive cells using the anti-Tac monoclonal antibodies would be of value in treating or controlling such pathological states.

The use of chemotherapeutic agents has cured some types of cancer. However, many types of cancer either are initially unresponsive or subsequently acquire resistance to chemotherapy. The development of monoclonal antibody technology by Kohler and Milstein (1975 Nature, 256:495) rekindled interest in the use of antibodies targeted to cell surface antigens to treat cancer patients. However, monoclonal antibodies are just beginning to fulfill the promise for immunotherapy inherent in their great specificity for recognizing and selectively binding to abnormal cells. A number of factors underlie the low therapeutic efficacy observed initially. Unmodified murine monoclonal antibodies are immunogenic and elicit a human immune response. Moreover, most of the mouse monoclonal antibodies used were not cytocidal against neoplastic cells in humans. Finally, in most cases the antibodies used were not directed against a vital cell surface structure such as a receptor for a growth factor that is required for both tumor cell proliferation and the prevention of apoptotic cell death induced by factor deprivation.

Adult T-cell leukemia is a malignancy of T lymphocytes with a median survival time of 9 months in the acute and 24 months in the chronic form of the disease. Various combination chemotherapies have not significantly increased the survival of patients with ATL. In light of the disappointing results using conventional combination chemotherapy, IL-2R-directed therapy was developed to exploit the observation that normal resting cells, including the unaffected normal T cells of patients with ATL, do not display IL-2Rα, whereas the leukemic cells express this interleukin receptor subunit.

Hodgkin's disease currently has an annual incidence of 4/100,000 in the United States. Tumors in the lymph nodes of affected patients are composed of nonmalignant lymphocytes far outnumbering the malignant Reed-Sternberg cells, which may express T or B cell markers. 40% of patients will have stage I or II disease, which is curable in >90% of cases with radiation and/or chemotherapy.

Non-Hodgkin's lymphoma is becoming more common in the U.S. The annual incidence, which does not include HIV-related cases, is about 15/100,000, over 30–60% higher than 12 years earlier. It is the most rapidly increasing cause of cancer death in white men and in white women is second only to lung cancer. T-cell varieties include cutaneous and peripheral T-cell lymphomas and lymphoblastic lymphoma. B-cell varieties are more common, and are divided into low, intermediate and high grades.

Peripheral T-cell leukemia/lymphomas including T-cell chronic lymphocytic leukemia (CLL) as well as Ki-1 lymphoma, also known as anaplastic large cell lymphoma, frequently expresses IL-2Rα on the surface of a significant proportion of the malignant cells. The malignant cells of between 21 and 47% of patients with HTLV-I negative peripheral T-cell lymphomas express IL-2Rα on the surface of the malignant cells. Furthermore, the malignant T cells in the skin and lymph nodes of patients with cutaneous T-cell lymphoma (mycosis fungoides and the Sézary syndrome) express the Tac antigen (or IL-2Rα). In addition, virtually all (>95%) of the malignant cells of patients with the hairy cell B-cell leukemia express the Tac antigen, and a proportion of other B-cell lymphomas are also Tac-positive. Finally, true histiocytic leukemias and the Reed-Sternberg cell of Hodgkin's disease also manifest the 55-kD Tac peptide. In addition to the expression of the Tac peptide on the surface of the malignant cells, a released soluble 45-kD form of the Tac peptide (referred to herein as "sIL-2Rα") appears in the circulation. Elevated concentrations of this soluble form of the IL-2 receptor are present in the circulation of patients with the Tac-expressing malignancies discussed above.

All of these diseases are treatable with the method of the present invention.

SUMMARY OF THE INVENTION

It is, therefore, an object of the present invention to provide a method of eliminating disease-associated Tac-positive cells.

It is a further object of the present invention to provide a method of treating conditions associated with elevated levels of Tac-antigen, such as adult T-cell leukemia ("ATL"), cutaneous T-cell lymphomas ("CTCL"), Peripheral T-cell lymphomas ("PTCL") and T-cell-mediated autoimmune disorders.

It is another object of the present invention to provide a method of treating B-cell malignancy.

It is another object of the present invention to provide a method of treating other leukemias and lymphomas associated with elevated levels of Tac antigen, such as true histiocytic leukemias, non-Hodgkin's lymphomas and Hodgkin's disease.

It is yet another object of the present invention to provide a method of controlling allograft rejection reactions, and graft-versus-host disease.

It is an object of the present invention to provide antibodies reactive with Tac antigen. In addition, it is an object of the present invention to provide a method of using Tac-antibodies to treat Tacassociated diseases.

It is a further object of the present invention to conjugate anti-Tac with agents capable of acting as cytotoxins, such as by radionuclide conjugation such as $^{212}$Bi or $^{90}$Y, or by toxin conjugation such as with *Pseudomonas* toxin or ricin A.

Other objects and advantages of the present invention will become apparent from the Detailed DESCRIPTION OF THE INVENTION

BRIEF DESCRIPTION OF THE DRAWINGS

These and other objects, features and many of the attendant advantages of the invention will be better understood upon a reading of the following detailed description when considered in connection with the accompanying drawings wherein:

FIG. 5. CAT scan of thorax of Patient 4 before treatment (top) and after two cycles of $^{90}$Y anti-Tac therapy (bottom). There was a marked reduction in the size of the axillary lymph nodes in the scan obtained during the period when the patient was in an $^{90}$Y anti-Tac therapy-induced partial remission.

FIG. 6. $^{111}$In anti-Tac imaging studies of Patient 1 prior to treatment and at the time of the fourth treatment with 90Y anti-Tac when the patient was in a complete remission. Prior to therapy $^{111}$In anti-Tac was deposited in sites of malignant T-cell infiltration of the skin of the hands, whereas no such deposition was evident at the time of the fourth study confirming the complete remission.

DETAILED DESCRIPTION OF THE INVENTION

Figure 1:
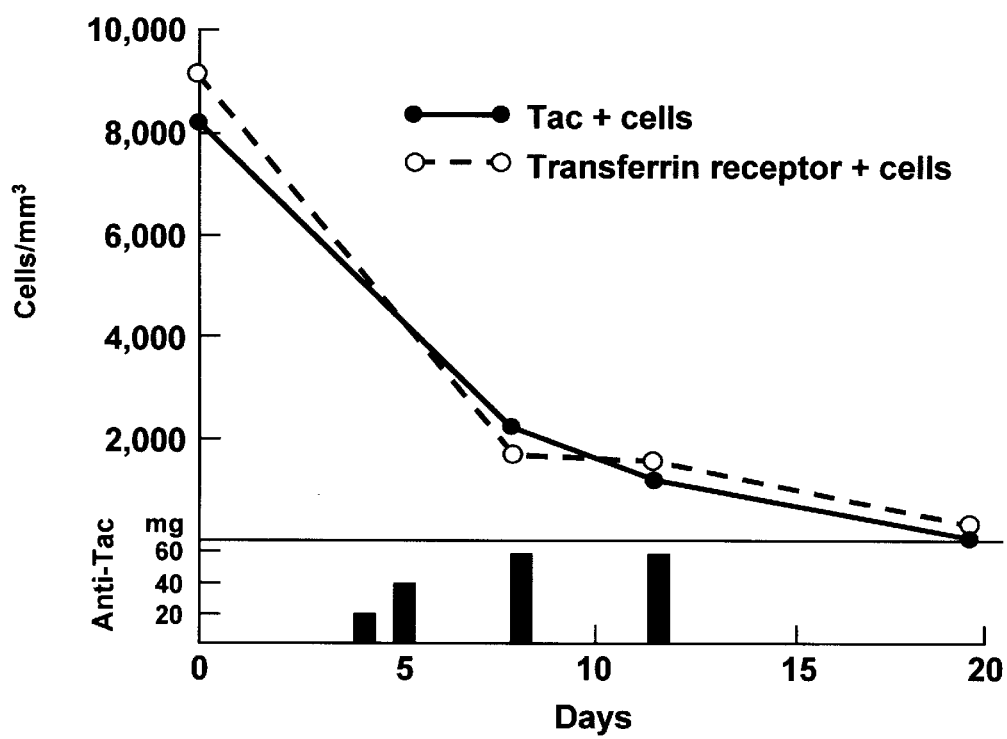
FIG. 1 shows the results of anti-Tac therapy of patient with Tac-positive ATL. The patient was treated with four infusions (20, 40, 50, and 50 mg) of anti-Tac monoclonal antibody over a 12 day period (indicated by solid bars). After the anti-Tac therapy, the number of circulating T cells bearing the Tac antigen declined from 8000 to less than 100/mm$^3$. There was a parallel decline of cells expressing another tumor-associated marker of the transferrin receptor from over 9000 before therapy to less than 100/mm$^3$.

The above and various other objects and advantages of the present invention are achieved by a method of treating disorders associated with Tac-positive cells in humans comprising administering to an afflicted human, a therapeutic amount of conjugated or unconjugated anti-Tac monoclonal antibodies to eliminate disease-associated Tac-positive cells without affecting normal cell populations.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated in toto by reference.

The methods of treatment described herein relate to diseases or conditions wherein Tac antigen is found in patients at "elevated levels". Elevated levels of Tac antigen are defined by several convenient parameters. The simplest definition for "elevated levels" of Tac is the case where more than 10% of a patient's peripheral blood mononuclear cells ("PMN") are Tac positive. Alternatively, a measure of sIL-2Rα can provide a normal level of sIL-2Rα as 235 units/ml. Here, elevated levels are defined as at least two (2) standard deviations above this mean value or a value greater than 504 units/ml of soluble IL2Rα.

Prior to the present studies, little was known about the inducible IL-2 receptor, and no antibodies to IL-2 receptor had been made. Using hybridoma technology, an IgG2a mouse monoclonal antibody called anti-Tac was prepared. This anti-Tac antibody reacted with activated but not resting T cells (Uchiyama et al, *J. Immunol.* 126:1393–1397, 1981; Uchiyama et al, *J. Immunol.* 126:1398–1403, 1981). Furthermore, this antibody identified the IL-2Rα receptor subunit and blocked IL-2 binding to its receptor (Leonard et al, *Nature* 300:267–269, 1981). The structure, function and expression of the IL-2 receptors on normal and malignant lymphocytes has been reviewed by Waldmann (*Science*, 232:727–732, 1986).

One embodiment of the present invention uses a humanized form of the murine anti-Tac which was developed in the present invention. Humanizing murine anti-Tac antibodies has been described by Queen et al. (1989 *Proc. Natl. Acad. Sci. USA* 86:10029), Junghans, et al. (1990 *Cancer Res.* 50:1495) and Brown, et al. (1991, *Proc. Natl. Acad. Sci. USA* 88:2663) and is incorporated herein by reference.

Based on the known unique properties of anti-Tac antibodies, a novel approach to immunotherapy was developed for the first time to eliminate leukemic cells and activated T cells in autoimmune disorders and in organ allograft protocols. These therapeutic studies were extended by coupling toxins to anti-Tac and showing that they killed tumor cells at doses that did not affect normal cells. Furthermore, anti-Tac was coupled to the alpha-emitting radionuclide such as bismuth 212 ($^{212}$Bi) or a β-emitting radionuclide such as yttrium-90 by the use of a bifunctional chelate. This agent was also shown to be an effective and specific immunocytotoxic agent for the elimination of IL-2 receptor-positive cells. The details of the procedure for the use of anti-Tac in the therapy of patients with adult T-cell leukemia and in organ allograft protocols are described below.

The present invention includes a therapeutic trial utilizing $^{90}$Y anti-Tac which was initiated to exploit the observation that the leukemic cells of patients in the IL-2-independent aggressive phase of their disease continued to express large numbers of the IL-2Rα receptor. When the 5- to 15-mCi doses were used, 9 of the 16 evaluable patients responded to $^{90}$Y anti-Tac with a partial or complete remission. The total quantity of anti-Tac administered in one embodiment of the instant invention was 2 to 10 mg of $^{90}$Y anti-Tac. The 18 patients in this 9 anti-Tac study were quite comparable to the previously studied 19 patients who were treated with unmodified anti-Tac (Waldmann, et al. 1993 *Blood*, 82:1701). In particular, the two groups were comparable in terms of age (mean age, 43 versus 41), ATL type (identical with the exception that there were two additional patients with lymphoma type ATL and one less with chronic ATL in the unmodified anti-Tac study), mean sIL-2R levels, number of circulating Tac-expressing lymphocytes, as well as incidence of hypercalcemia, abnormal liver function tests, and immunodeficiency.

Figure 7A:
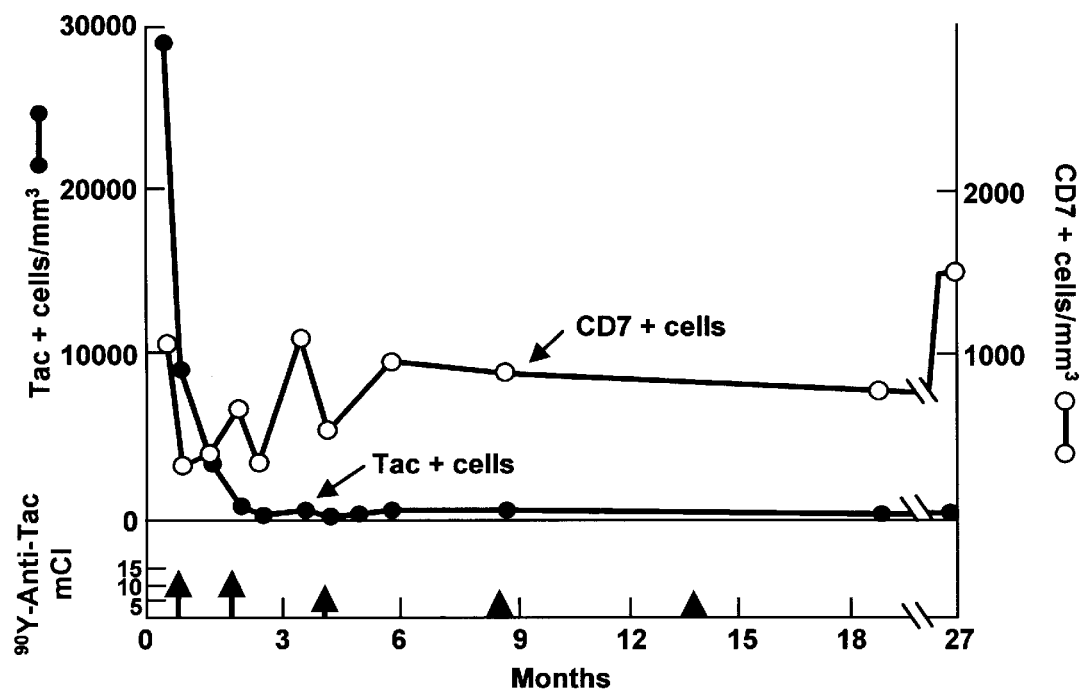
FIG. 7. (A) Effect of $^{90}$Y anti-Tac therapy on the absolute number of Tac-expressing ATL leukemic and normal T cells/mm$^3$ of Patient 7. $^{90}$Y anti-Tac monoclonal antibody was administered i.v. to the patient at the doses and on the days indicated by the arrows (→). The patient initially had 27,875 circulating Tac-expressing malignant cells/mm$^3$(- •) The patient received 50 mCi of 90Y anti-Tac during the first 410 days of therapy in divided doses. By day 300 following initiation of therapy, the patient had undergone a complete remission that has been maintained for the over 800-day period of observation. There was an initial modest reduction in the number of normal T cells (O—) (normal T cells are CD7$^+$CD25$^-$). However, the number of these normal T cells subsequently returned to pretreatment levels during the remaining period when the patient was in a sustained complete remission. (B) Effect of $^{90}$Y anti-Tac therapy on the serum concentration of sIL2Rα of the same patient. The serum sIL-2Rα level of the patient prior to therapy was 2,938 units/ml. The concentration sIL-2Rα returned to normal or below normal levels following therapy confirming the complete remission.
Figure 7B:
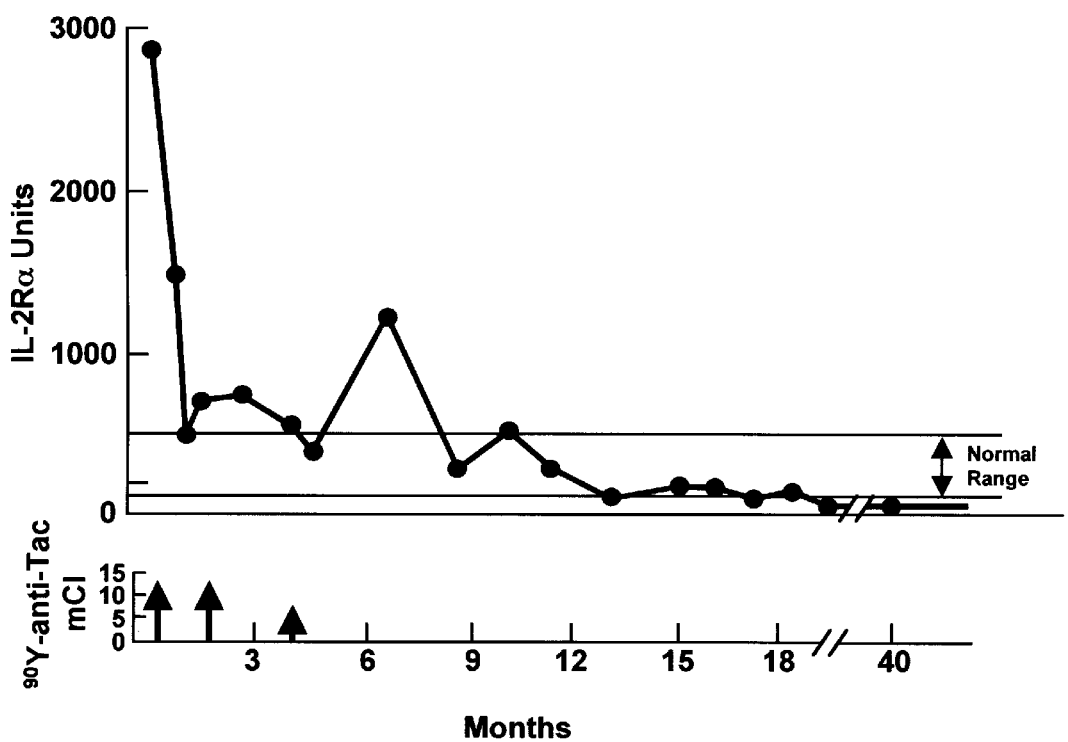

The response to therapy with either unmodified or $^{90}$Y-labeled anti-Tac correlated with the disease classification and response to previous chemotherapy. In particular, seven of the nine patients in the two studies with chronic ATL developed a partial or complete remission. Eight of the 22 patients with acute or lymphoma type ATL who were not failing an ongoing course of chemotherapy manifested a remission, whereas no remissions were observed in the six patients who were studied within 1 to 2 months of completion of an ineffective course of aggressive chemotherapy. A Kaplan-Meier (1958 *J. Am. Stat. Assoc.*, 83:457) plot of event-free survival (surviving patients without aggressive disease) comparing patients treated using unmodified anti-Tac with those receiving $^9$Y-labeled anti-Tac is presented in FIG. 7. $^{90}$Y-labeled anti-Tac therapy suggests improved efficacy (P<0.029) when compared to treatment with unmodified murine anti-Tac. However, it should be noted that this comparison must be viewed with caution since the patients were not studied simultaneously in a randomized controlled trial.

Another embodiment of the present invention provides an alternative treatment regime for patients and begins with a 2–10 mg dose of $^{90}$Y-conjugated anti-Tac, wherein 0.5–15 mCi $^{90}$Y is provided. Thereafter, a second treatment is provided comprising a 75–150 mg dose of unconjugated anti-Tac. Such a two-step treatment scheme assures maximum saturation of IL-2Rα sites in a patient.

A variety of methods for administering Tac antibodies are available and well-known in the art. Among the methods which can be employed in the present invention are intravenous, subcutaneous and intramuscular. Other methods useful in the present invention would be clear to the skilled artisan.

Antibodies of the present invention can be of various types. Polyclonal anti-Tac as well as monoclonal antibodies can be used in the various treatment regimes disclosed herein. Murine antibodies and humanized forms of antibodies can be used in the present invention. Other sources of antibodies, including, but not limited to porcine, bovine, avian and human can be used in treatment of patients as set forth in the present invention.

Further, it is understood that portions of antibodies may be used in the present invention, such as a single chain of an immunoglobulin or Fab or Fv portions of the anti-Tac antibody may be used.

Based on in vivo pharmacokinetic and bioavailability studies during the Phase I trial using $^{90}$Y-anti-Tac we developed an algorithm to predict a dose of total anti-Tac (sum in mg of unlabeled and labeled antibody) that was sufficient to overcome the effect of soluble antigen levels (i.e., sIL-2R), without excessively diluting antibody-specific activity (see Example 17). Based on this algorithm, the nine patients in the Phase II $^{90}$Y anti-Tac trial received a total quantity of anti-Tac in their initial treatment or retreatment cycle that was determined by their soluble serum IL-2R levels. Patients with a sIL-2R of under 2,000 units/ml received a total dose of 2 mg of anti-Tac, those with 2,000 to 10,000 units/ml received 5 mg of anti-Tac, and those with over 10,000 units/ml received 10 mg of anti-Tac.

In the 40 years since Korngold and Pressman (1954 *Cancer Res,* 14:96) used $^{131}$I-labeled antibodies to localize tumors in rodents, numerous clinical trials have been performed using radiolabeled monoclonal antibodies for the therapy of cancer. Many of the therapeutic trials have been performed in patients with solid tumors. The results have been discouraging and generally have not resulted in clinically significant responses. Therapy of leukemia has generally been more encouraging with several studies reporting clinical responses. The results using $^{90}$Y anti-Tac in the treatment of ATL reported in one embodiment of the present invention also are of great value. Thus, it may be of further value to consider the various elements contributing to the remissions. Such an analysis may be useful in designing new strategies involving receptor-directed radioimmunotherapy in diverse clinical circumstances.

Factors that appear critical in developing an effective radioimmunotherapeutic regimen include (a) the choice of radionuclide; (b) the selection of the chelate used to link the radionuclide to the monoclonal antibody; (c) the choice of the monoclonal antibody; and (d) the definition of the optimal quantity of monoclonal antibody to be administered. Nuclear chemistry has provided a selection of radionuclides that can be linked to immunoproteins. An appropriate choice of radionuclide would be one that has a short distance of action (e.g., one with a β or β emission) that will thereby maintain the antigen specificity of the monoclonal antibody and kill antigen-expressing tumor cells and a few adjacent antigen nonexpressing cells but will spare distant normal cells. β-emitting radionuclides, such as $^{131}$I, $^{90}$Y, $^{186}$Re, $^{188}$Re, and $^{67}$Cu, have been useful in immunotherapy. Yttrium-90 has a high β-energy emission (2.29 MeV maximum, 0.94 MeV average) and has a desirable 64-hour half-life. Yttrium-90 is attractive for therapy of lymphoma since it decays with high-energy beta but no gamma emissions. The energy released per unit of activity is approximately five times greater than that of $^{131}$I and would yield a significantly higher radiation dose delivered to the tumor. The high-energy beta emission of $^{90}$Y may be of special value for large tumors, including malignant lymph nodes, because this emission manifests greater tissue penetration than the low-energy beta emission of $^{131}$I. Therefore, $^{90}$Y-labeled monoclonal antibodies can kill nontargeted antigen-nonexpressing tumor cells through a "crossfire" effect from neighboring antigen-expressing cells that have been targeted by the radiolabeled monoclonal antibody.

A second pivotal issue in designing an optimal radioimmunotherapeutic reagent is the choice of the method used to link the radionuclide to the monoclonal antibody. In the case of metals, it is critical that the chelate retain the radiometal tightly and not permit its release from the monoclonal antibody chelate complex in vivo. This is especially important for $^{90}$Y because it is a bone seeker. That is, any 90Y released into the circulation would be rapidly cleared into bone and would produce undesirable irradiation of the bone marrow, the critical organ. We chose 1B4M-DTPA as our chelate based on our previous study where we compared the in vivo stability, in mice, of seven radioimmunoconjugates that used different polyaminocarboxylate chelating agents to complex radioyttrium to anti-Tac (Kozak, et al. 1989 *Cancer Res.* 49:2639). Another useful chelating agent used in conjugation is 2-(P-isothiocyantobenzyl)-trans-cyclohexyldiethylenetriamine penta-acetic acid (CHX-A). This reagent is particularly useful in preparing $^{212}$Bi anti-Tac conjugates. A number of the chelating agents evaluated, including those that have been used in other immunotherapeutic trials (e.g., ethylenediaminetetraacetic acid) provided unstable coupling of the radioyttrium to the antibodies. In contrast, the lB4M-DTPA chelating agent chosen for use in the present study emerged as promising immunotherapeutic reagents since it behaved essentially identically to co-administered radioiodine-labeled antibody and was associated with only a modest accumulation into bone of the injected radioyttrium (1.4 to 1.8 percent of i.v. dose/g). Thus, the chelating agent used in this embodiment of the present invention is stable in vivo and suitable for yttrium monoclonal antibody radioimmunotherapy.

A third critical component to consider is the selection of the monoclonal antibody that serves to carry the radionuclide to the tumor target. A monoclonal antibody is selected in part based on the distribution of its antigenic target and on the specificity and binding affinity of the antibody to its target. In the present invention we selected anti-Tac because of its ability to bind to the interleukin-2 receptor alpha subunit, a subunit that is not expressed on resting normal cells but is expressed on the surface of a number of leukemic cells, including the HTLV-1-associated ATL. An additional feature that may be critical in developing an effective agent for radiolabeled monoclonal antibody treatment is to choose an antibody that in its unmodified state has an antitumor effect, especially one that involves induction of apoptosis in sensitive tumor cells either by depriving the cells of a required growth factor or by acting as an agonist of a negative signaling pathway. An antibody that induces apoptosis may work synergistically with protracted low-dose irradiation to kill tumor cells.

The efficacy observed in one embodiment of the present invention with $^{90}$Y anti-Tac may be due in part to the fact that anti-Tac inhibits the interaction of the growth factor IL-2 with the high-affinity IL-2 receptor expressed on ATL cells. Such withdrawal of IL-2 action has been shown to activate an apoptotic suicide program in IL-2-dependent T cells (Duke, et al. 1986 *Lymphokine Res.* 5:289). This may be the critical element in the therapeutic action of unmodified anti-Tac in the subset of patients that have leukemic cells that still produce and respond to IL-2. In the present 90Y anti-Tac treatment, it is possible that several different antitumor mechanisms are working in concert, including low-dose irradiation coupled with antibody induced apoptosis.

An additional factor that is critical in the design of effective therapeutic trials concerns the definition of quantity of administered antibody (sum of radiolabeled and unmodified antibody) that delivers the highest proportion of the administered radiolabeled monoclonal antibody to the surface of the target cells, in our case IL-2R expressing tumor cells. This is not achieved by administering the radiolabeled antibody at the highest possible specific activity, nor is it achieved by administering sufficient monoclonal antibody to saturate all receptor targets.

When small quantities of radiolabeled antibody were administered to patients with high sIL-2Rα levels, the administered radiolabeled antibodies formed complexes with circulating sIL-2R and were no longer able to bind to target tumor cells efficiently. At the other extreme, if a large total quantity of antibody is administered, the tumor cell surface receptor sites become saturated and much of the radiolabeled antibody remains in the plasma and other extracellular body fluids unbound to tumor cells, thereby both reducing the proportion of the administered radioactivity delivered to the tumor cell and increasing the radiation delivered to normal tissues. Based on our pharmacokinetic and bioavailability data we have derived a relationship to predict a dose of total anti-Tac in milligrams that is sufficient to overcome the blockade to tumor cell binding caused by circulating specific soluble antigen (sIL-2R) levels, yet does not dilute the antibody radioactivity excessively, thereby yielding a therapeutic regimen with improved antibody bioactivity, cell binding, and targeting of radioactivity to tumor for imaging and therapy.

Although murine monoclonal antibodies including murine anti-Tac are of value in the therapy of certain diseases, their effectiveness is limited because rodent monoclonal antibodies induce an immune response that neutralizes their therapeutic effect. To address the immunogenicity of the murine monoclonal antibody, we constructed a humanized antibody by combining the complementarily-determining regions of the murine anti-Tac antibody with human IgGI kappa framework and constant regions. The humanized version of anti-Tac was dramatically less immunogenic than murine anti-Tac when administered to cynomolgus monkeys who received heterotopic cardiac allografts. Furthermore, none of 18 patients with graft-versus-host disease (referred to as "GVHD") and only 1 of 6 with lymphoma who received unmodified humanized anti-Tac made antibodies to the infused monoclonal antibody. This observation, taken in conjunction with the clinical study of the invention utilizing $^{90}$Y-murine anti-Tac suggested our active study that involves the use of $^{90}$Y-humanized anti-Tac in conjunction with G-CSF to treat ATL. The present invention extends the range of patients who would receive $^{90}$Y-humanized anti-Tac beyond ATL patients. This treatment may also be used in conjunction with other agents, such as in conjunction with G-CSF (also called "granulocyte colony stimulating factor").

Several non-Adult T-cell lymphoma diseases can be treated with anti-Tac therapy. One such disease is cutaneous T-cell lymphoma (CTCL) which is variably used either to represent only the two clinicopathologic entities: mycosis fungoides and Sézary syndrome or to also encompass other entities such as cutaneous lymphoblastic lymphoma and diffuse lymphomas of the skin which have T-cell surface markers (peripheral T-cell lymphoma). Here we use the term CTCL to include mycosis fungoides and Sézary syndrome and will discuss the other entities separately.

Another non-Adult T-cell lymphoma treatable with anti-Tac therapy is Peripheral T-cell Lymphoma ("PTCL"). PTCL is a diverse group of malignancies whose common unifying factor is their origin from a T-cell with cell surface markers indicating a post-thymic stage of maturation. Mycosis fungoides and Sézary syndrome, although they meet this criteria, are generally considered separately because of their distinct clinical features. Therefore, the definition includes Lennert's lymphoma, angioimmunoblastic lymphoma, angiocentric type PTCL, Tzone lymphoma, large cell anaplastic (Ki-1) lymphoma and other so-called specific and non-specific types of PTCL. For the purposes of the present invention, we will also include T-cell prolymphocytic and T-cell CLL in this group. Collectively these disorders represent 10–30% of non-Hodgkin's lymphomas diagnosed in the United States.

As noted above, $^{90}$Y-anti-Tac therapy may be administered in conjunction with other agents, such as G-CSF. In light of the hematopoietic toxicity associated with high dose $^{90}$Y-anti-Tac administration in monkeys, G-CSF was administered in conjunction with $^{90}$Y-anti-Tac in an effort to reduce the hematopoietic toxicity in a preclinical cynomolgus monkey cardiac allograft transplantation model. In this model system for the present invention, the granulocytopenia and consequent mortality was reduced in a group of animals receiving G-CSF administered concomitantly with $^{90}$Y-anti-Tac when compared to a group receiving the same dose of radiolabeled anti-Tac alone. Both sets of animals received 1.6 mCi/kg of $^{90}$Y-anti-Tac divided over 4 doses. In animals receiving radiolabeled anti-Tac alone, there were 3 deaths among 5 animals treated. In contrast, there were no deaths of animals receiving G-CSF in conjunction with the same dose of $^{90}$Y-anti-Tac. The most severe and most biologically meaningful toxicity was a reduction in the number of circulating white blood cells, including granulocytes. The administration of G-CSF was associated with a reduced severity and a shortened duration of the neutropenia. The mean nadir for total white blood cell count concentration was 1,000±400/mm$^3$ for the animals receiving G-CSF in addition to radiolabeled antibody. The mean nadir value for neutrophils was 338 in the group receiving the radiolabeled antibody alone, as compared to 1,778 in those receiving G-CSF as well (P<0.03). The administration of G-CSF did not affect the lymphocyte levels nor did it interfere with the efficacy of $^{90}$Y-anti-Tac in preventing early allograft rejection. In light of these observations, we plan to administer G-CSF to treat granulocytopenia caused by $^{90}$Y-labeled anti-Tac in the present protocol.

The present $^{90}$Y-anti-Tac therapy permits the administration of as many as 9 doses of $^{90}$Y-anti-Tac over a single treatment course. Of course, multiple courses of treatment may be necessary if symptoms recur or the patient relapses. One patient with ATL has received 9 doses of $^{90}$Y-anti-Tac and is a sustained complete remission. Another patient with ATL is still receiving courses of $^{90}$Y-anti-Tac. The remaining 18 patients did not receive all 9 doses. In many of these cases the variance in dosage treatments is reflected by the development of progressive disease or hematopoietic toxicity. In 4 cases however following induction of a partial or complete remission, the patients produced antibodies to the mouse monoclonal antibody ("HAMA").

In one embodiment of the present invention, $^{90}$Y-humanized anti-Tac will be used instead of $^{90}$Y-murine anti-Tac. $^{90}$Y-humanized anti-Tac, is also used in treating patients with ATL. Twenty-four patients have received unmodified humanized anti-Tac, 18 with steroid-resistant GVHD and 6 with lymphoma. There has been no toxicity observed following the administration of this material.

Furthermore, cynomolgus monkeys were treated for 4 weeks with daily intravenous injections of humanized anti-Tac at three dose levels: 1.5, 5.0, and 15 mg/kg. The animals exhibited no obvious treatment-related adverse clinical or laboratory abnormalities. The doses in milligrams of humanized anti-Tac (referred to herein "anti-Tac-H") involving patients with GVHD are higher than those proposed in this embodiment of the present invention. The reasons for this difference is that unmodified anti-Tac-H is used in the GVHD study, whereas anti-Tac-H armed with $^{90}$Y was used in one embodiment of the present invention to treat patients with post-thymic T-cell malignancies. When unmodified anti-Tac-H is used, the objective is to administer sufficient antibody to saturate all IL-2 receptors. Large quantities of antibody increase effectiveness. In contrast, when $^{90}$Y-anti-Tac-H is used as in the present embodiment, the goal is to deliver high-specific-activity $^{90}$Y to the surface of the malignant cells. The antibody is the delivery system rather than the effector of treatment in this case. Increased total doses of anti-Tac-H in milligrams would lead to a reduced specific activity for a given quantity of $^{90}$Y (e.g., 10 mCi), thereby reducing the proportion of the administered therapeutic dose delivered tb the tumor cells with a consequent reduction in the therapy-totoxicity ratio observed.

All patients in the present clinical study receive $^{90}$Y-anti-Tac-H intravenously. However, alternative methods of administration are well-known in the art and can be used in the present invention. In select patients, up to 5 mCi of $^{111}$In anti-Tac-H on up to three occasions are coinjected with $^{90}$Y-anti-Tac-H using the same chelate to obtain tissue activity estimates by nuclear scans. The gamma radiation from $^{111}$In allows adequate visualization of tumor and tissue uptake thereby compensating for the poor quality images expected from $^{90}$Y, a pure beta emitter. It should be noted that, in some cases, tissue biopsies may be obtained to compare $^{111}$In and $^{90}$Y directly and to validate the assumption that $^{111}$In distribution is a good tracer for dosimetry purposes. Imaging techniques may be used at multiple times to determine the quantitative spatial distribution and the residence times for the radionuclide in tumor sites and in critical organs.

One embodiment of the present invention evaluates an initial administration of the 10-mCi dose of $^{90}$Y-anti-Tac-H followed in a given patient by up to 6 additional 5-mCi doses. The goals of the trial are to determine toxicity as well as efficacy in a group of 30 patients with CTCL and 30 with PTCL. On the basis of the studies using murine anti-Tac, the radiation-associated toxicity is anticipated to be manifested predominantly by bone marrow depression. Because of the high dose or radiation to normal organs a higher risk of second malignancy is possible; the additional risk, beyond that already present, for a second malignancy is unknown. To treat the therapy-associated granulocytopenia, administration of G-CSF at 5 µg/kg/day to patients whose polymorphonuclear leukocytes fall below 1,000/mm$^3$. The G-CSF may be administered at this dose (for up to 45 days) until the PMN count increases to greater than 10,000/mm$^3$. This dose of G-CSF was effective in reducing the magnitude and duration of the granulocytopenia observed in cynomolgus monkeys receiving $^{90}$Y-anti-Tac. Numerous blood and urine samples may be collected in order to quantitate the rates of clearance of the radionuclide and antibody and to monitor for the development of antibodies to the infused humanized anti-Tac. Skin biopsies of evident lesions, bone marrow aspirates/biopsies, and lymph node biopsies may be performed as outlined to help establish optimal non-invasive dosimetric parameters.

In yet another embodiment of the present invention, the cytotoxic agent Pseudomonas exotoxin (referred to as "PE") is conjugated to anti-Tac.

Five (5) patients with T-cell leukemia were treated with anti-Tac-PE. The patients were treated intravenously with doses of 0.2 to 2.0 mg for a total dose of up to 4.4 mg over 1 week. Two of the five patients developed Grade III or IV hepatotoxicity with one manifesting a transient elevation of the hepatic transaminases (SGOT & SGPT) to levels of 1000–1200 units/1 and the other patient having a rise in the bilirubin from normal to 4.1 mg/dl. Neither of these reactions was associated with clinical symptoms and in both patients the abnormalities remitted within two weeks of stopping treatment. None of the five patients manifested a clinically apparent tumor response.

To target cells with a single-chain protein containing the antigen binding domains of anti-Tac, the variable domains of the antibody ($V_H$ and $V_L$) were fused together with the peptide linker $(G_4S)_3$ and the resulting Fv fragment of anti-Tac was fused to PE40 as described in Chaudhary, et al. 1989 Nature, 339:394, which is incorporated herein by reference. Anti-Tac(Fv)-PE40 was extremely cytotoxic with an IC$_{50}$ of 0.15 ng/ml toward HUT102 cells and 0.05–0.1 ng/ml toward activated human Tcells. To determine if malignant cells in patients have enough receptors and metabolize the toxin effectively enough to be sensitive to anti-Tac(Fv)-PE40, we tested ATL cells from the blood of 38 patients and from the lymph nodes of 5 patients. All samples were sensitive to anti-Tac(Fv)-PE40, with IC$_{50}$'s of 0.03–16 ng/ml. Anti-Tac(Fv)PE40 was shortened slightly by removing amino acids 365380, resulting in anti-Tac(Fv)-PE38. The cytotoxic activity of anti-Tac(Fv)-PE38 appears identical to that of anti-Tac(Fv)-PE40 toward cell lines and fresh ATL samples. The details of anti-Tac(Fv)-PE38 synthesis are set forth in Kreitman, et al. (1993 Bioconjug. Chem., 4:112) which is incorporated herein by reference.

A mouse model of a human IL2Rα positive malignancy was produced by the subcutaneous injection in nude mice of ATAC-4 cells as described by Kreitman, et al. (1994 Blood, 83:426). These cells are A431 epidermoid carcinoma cells that have been transfected with the gene encoding IL2Rα, and contain 2×10$^5$ IL2Rα sites/cell. Mice began treatment with anti-Tac(Fv)-PE38 4 days after ATAC-4 cell injection, when subcutaneous tumors became established (32–86 mm$^3$). 90–100% tumor regressions were observed in 2 to 5 mice receiving 30 µg/Kg i.v. QD X3, and in 5 of 5 mice receiving 60 µg/Kg i.v. QD X3. "QD X3" as used herein refers to administering treatment every day for a total of 3 doses. These doses were respectively 5 and 10% of the mouse LD$_{50}$. When administered to mice every other day, complete tumor regressions could be obtained in 5 of 5 mice receiving 100 µg/Kg i.v. QOD X3, and the LD$_{10}$ and LD$_{50}$ were both ~300 µg/kg i.v. QOD X3). "QOD X3" as used herein refers to administering treatment every other day for a total of three (3) doses.

Cynomolgus monkeys were used to determine the safety and pharmacokinetics of anti-Tac(Fv)-PE38, since anti-Tac reacts with primate but not murine IL2Rα. In one pharmacokinetics study, the elimination of anti-Tac(Fv)PE38 from the serum followed biphasic kinetics, with a $T_{1/2}\alpha$ of 16 minutes and a $T_{1/2}\beta$ of 140 minutes. In a toxicology study, 4 cynomolgus monkeys received 20 µg/kg QOD X3 without significant toxicity. Four monkeys were administered 300 µg/kg QOD X3, and experience anorexia combined with mild (2 to 5-fold) transaminase elevations. One of two monkeys autopsied in this high-dose group had hepatomegaly and mild diffuse hepatocyte vacuolation.

EXAMPLE 1

Treatment of ATL with Unmodified Anti-Tac

Patients with adult T-cell leukemia (ATL) are treated by intravenous infusions of unmodified anti-Tac. ATL is an aggressive leukemia of polymorphic mature T cells with a propensity to infiltrate the skin. This leukemia is frequently associated with hypercalcemia and pulmonary involvement. The leukemic cells always contain the C-type retrovirus Human T-Cell Lymphotrophic Virus I (HTLV-I). There is no curative therapy for patients with ATL, and such patients have a mean survival time of only about 20 weeks. In contrast to normal cells, the malignant cells of patients with ATL display the cell surface receptor for interleukin-2 identified by the anti-Tac monoclonal antibody.

The anti-Tac murine-derived monoclonal antibody used for these therapeutic studies has been produced by fusing NS-1 cells with spleen cells of mice immunized with a cell line derived from an ATL patient. Large quantities of the monoclonal antibody are produced by inoculating hybrid cells into the peritoneum of BALB/c mice and purifying this IgG2a K antibody from the resulting ascites fluid by DEAE chromatography with elution by 0.1 Tris buffer as the eluting agent. The material is dialyzed against saline, centrifuged, filtered, precipitated with 20% sodium sulfate, and then diluted in saline at pH 7.4 to a concentration of about 2 mg/ml. Each lot of the product is shown to be pure by assays that include immunoelectrophoresis, diffusion in agar plates using antisera to IgG2a, IgG1, IgM, and transferrin, as well as polyvalent antibodies to major mouse proteins. Furthermore, the lots are shown to be homogenous by HPLC. The monoclonal preparations are sterilized by passage through a 0.22 millipore filter and are shown to be nonpyrogenic and sterile. Patients with Tac-expressing ATL receive anti-Tac antibody by intravenous administration of a dose in 100 cc of normal saline with 5% human albumin over a 2-hour period. Patients receive anti-Tac at a higher dosage each week for 2 weeks. During the first week, they receive two doses of 20 mg per patient and, in the second week, two doses of 50 mg per patient. Patients undergoing partial or complete remission or those with leukemic cells with persistent Tac receptors unblocked by the anti-Tac monoclonal antibodies may receive additional biweekly doses of 50 mg of anti-Tac. Unblocked IL-2 receptors can be identified with flow cytometry using fluorochrome-labeled anti-Tac monoclonal antibodies using conventional procedures.

Figure 2:
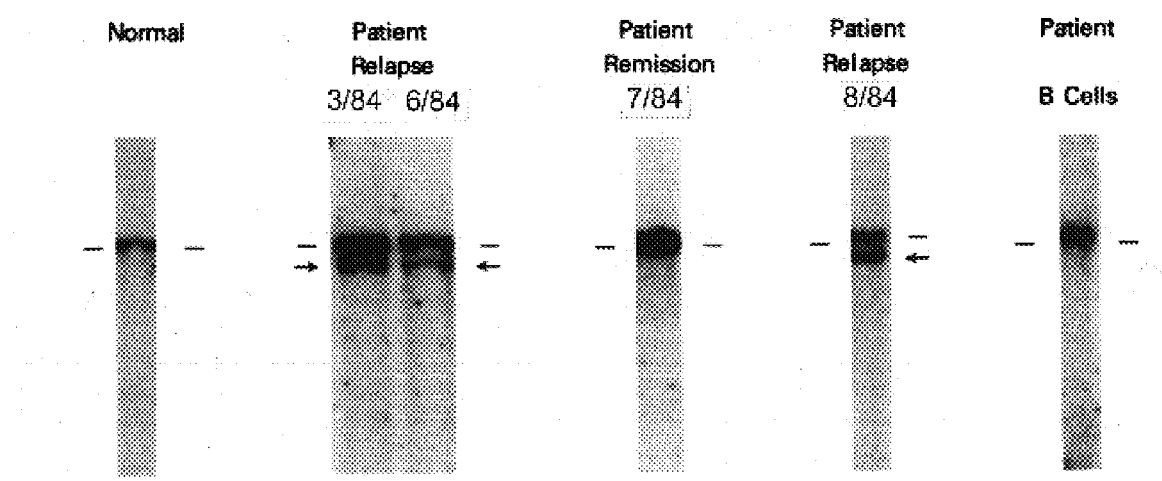
FIG. 2 shows the effect of anti-Tac therapy on CT β chain gene arrangement in a patient with ATL. The remission of the T-cell leukemia in this patient after anti-Tac therapy was confirmed using molecular genetic analysis of the arrangement of the genes encoding the β chain of the antigen-specific T-cell receptor. Southern analysis of the arrangement of the T-cell receptor β chain was performed on BamHI digests of DNA from the peripheral blood mononuclear cells of the patient by using a radiolabeled probe to the constant region of the T β chain. The constant T β genes are universally present on a 240 kb BamHI fragment in germline tissues of normal individuals and in a B-cell line from the patient. However, before therapy there was an additional 22-kb BamHI band hybridizing with the constant T β probe when digests of the patient's circulating T cells were examined, a hallmark of a clonal expansion of T lymphocytes. This band reflecting the clonally rearranged T-cell receptor gene was not demonstrable on specimens obtained after anti-Tac therapy when the patient was in remission. Six months after the initial remission the leukemia recurred with reappearance of leukemic cells identified by a molecular genetic analysis. A second course of infusions of anti-Tac was followed by a virtual disappearance of the skin lesions and the circulating leukemic cells (data not shown)
Figure 3:
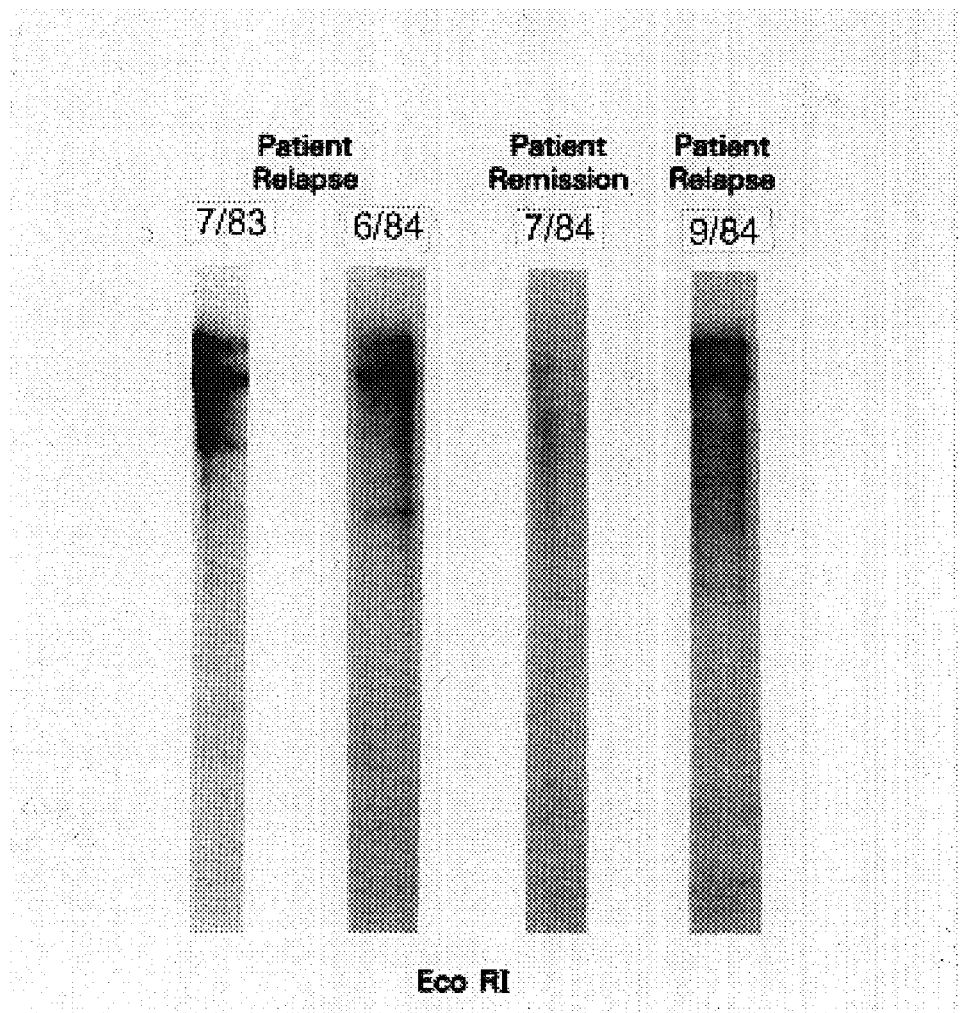
FIG. 3 shows the effect of anti-Tac therapy on leukemic mononuclear cells with integrated HTLV-I. HTLV-I is clonally integrated into the cells of patients with HTLV-1-associated ATL. Such integrated HTLV-I can be identified by Southern analysis using a radiolabeled HTLV-I probe. In the case shown, there are two lines on the Southern gel indicating the integration of two HTLV-I viruses per cell. After anti-Tac therapy, the circulating cells of this patient did not contain integrated HTLV-I as shown by the clear Southern gel autoradiograph. After recaps, integrated HTLV-I could again be demonstrated in the circulation T cells.

Ten patients with ATL have been treated with intravenously administered anti-Tac monoclonal antibody according to the above protocol. None of the patients suffered any untoward reactions or produced antibodies to mouse immunoglobulin or to the idiotype of the anti-Tac monoclonal. There was no reduction in the number of any of the normally formed elements of the blood. Three of the patients had a reduction in the number of circulating leukemic cells or a complete remission after anti-Tac therapy. In one of these patients, therapy was followed by a 5-month remission as assessed by routine hematological tests, immunofluorescence analysis of circulating T cells (FIG. 1), molecular genetic analysis of the arrangement of the genes encoding the # chain of the T-cell receptor (FIG. 2), as well as the genes of the retrovirus HTLV-2 (FIG. 3). After the 5-month remission, the patient's disease relapsed, but a new course of anti-Tac therapy was followed by a virtual disappearance of the skin lesions and an over 80% reduction in the number of circulating leukemic cells.

Treatment of ATL with Anti-Tac Conjugated with Cytotoxic Agents

EXAMPLE 2

Anti-Tac Antibody Coupled to Ricin A Chain

Using conventional procedures, purified anti-Tac monoclonal antibody is conjugated to purified or recombinant ricin A chain using a thiol-containing crosslinker, N-succinimidyl-3-(2-pyridyldithio)propionate (Kronke et al Blood 65:1416–1421, 1985). The resulting conjugates are separated from the majority of free ricin A chains by Sephacryl S-200 gel filtration. Conjugates are adjusted to 1 mg/ml with reduced and alkylated human IgG and stored at −20° C. The addition of carrier protein assures stability of the conjugates, and the alkylation prevents disulfide toxin exchange between specific antibody and carrier protein. The addition of anti-Tac antibody coupled to the A chain of the toxin (ricin) effectively inhibited protein synthesis and led to cell death of an HTLV-I-associated, Tac-positive ATL cell line, HUT102-B2. In contrast, conjugates of ricin A with a control monoclonal of the same isotype did not inhibit protein synthesis when used in the same concentration. The inhibitory action of anti-Tac conjugated with ricin A could be abolished by the addition of excess unlabeled anti-Tac or IL-2.

EXAMPLE 3

Anti-Tac Coupled to Pseudomonas Toxin

The immunotoxin *Pseudomonas* exotoxin anti-tac is made from purified pyrogen-free anti-Tac and purified *Pseudomonas* exotoxin (PE) according to published methods (Fitzgerald et al. *Proc. Natl. Acad. Sci. USA* 80:4134–4138, 1983). Two mg (30 nM) of PE in $KPO_4$ 0.1 M, EGTA 1 mM, pH 8.0, is incubated with 500 nM of NAD and 5000 nM of 2-iminothiolane-HCl for 1 hour at 37° C. NAD is added to protect the enzyme-active site of the toxin. This derivatized PE preparation is separated on HPLC from a small amount of aggregated toxin by the other reactants. Dithio-bis(2-nitrobenzoic acid) (DTNB) is added to the derivatized PE to a final concentration of about 1 mM. The addition of DTNB and its reaction with free sulfhydryl groups serves to activate the toxin for future disulfide exchange with antibody.

The antibody (5–8 mg) in $KPO_4$ 0.1 M, EGTA 1 mM, pH 8.0, is incubated with 120 nMol of 2-iminothiolane-HCL for 1 hour at 37° C. At the end of the incubation period, the antibody is separated from iminothiolane by gel filtration on a G-25 column. An aliquot of the derivatized antibody is reacted with DTNB to determine the number of new sulfhydryl groups introduced. The remainder is mixed with the activated PE. Activated PE is reacted with derivatized anti-Tac antibody. The reaction is followed by measuring the release of TNB (thionitro-benzoic acid-nitrophenol) at $OD_{412}$. The antibody-SH releases routinely half of the TNB from the activated PE molecules. The balance is released by adding excess cysteine. The reaction mixture is separated by HPLC. The PE-antibody-$(cys)_2$ has the most activity and is used for patient therapy. The PE-anti-Tac is stored at −20° C. in 0.15 M NaCl, 10 mM $KPO_4$, 1 mM EGTA, pH 7.2.

Patients with ATL received PE-anti-Tac antibody by intravenous administration in 100 cc of normal saline with 1% albumin over 2 hours. Each patient received about 200 µg of PE-anti-Tac twice during the first week and 2 mg twice a week during the second week. Therapy was stopped if the patient manifests grade III hepatic toxicity, that is, a bilirubin over 3.0 mg/ml or an SGOT or alkaline phosphatase 3–5 times the base line.

Four patients have been treated with PE-anti-Tac according to this protocol. One of the four patients manifested hepatic dysfunction, including abdominal pain and a transient disorder of the liver function tests. One of the patients had a response to the PE-anti-Tac therapy manifested by an over 50% decline in the number of circulating leukemic cells.

It is noted that other cytotoxic conjugates of anti-Tac can be similarly prepared and used. The examples provided herein being only exemplary.

EXAMPLE 4

Treatment Regimen Using Pseudomonas Toxin Anti-Tac Conjugate

Three patients are accrued at each dose level starting with one group at 10 µg/kg QOD×3 and increasing to groups of three patients receiving 20 µg/kg, 40 µg/kg, 65 µg/kg, 100 µg/kg, and then in groups that receive doses that escalate at 50 µg/kg intervals until one patient in the treatment group develops a Grade III toxicity. "QOD X3" as used herein refers to administering treatment every other day for a total of 3 doses. All groups will receive the dose indicated QOD×3. In addition, all patients will receive a 10 µg test dose diluted in 0.9% NaCl and 0.2% albumin, given as a bolus prior to each cycle. The immunotoxin will be infused in 50 ml of 0.9% NaCl and 0.2% albumin via a PAB container over 30 minutes. Vital signs will be obtained every 15 minutes during the infusion, then every 30 minutes for the next 2 hours then every hour for 4 hours, then as per unit routine. Medications and equipment are available at the patients bedside for treatment of an allergic reaction (epinephrine, $O_2$, diphenhydramine).

Patients without evidence of progression and without neutralizing antibodies may receive up to 9 further cycles of anti-Tac(Fv)-PE38 at the same dose with at least 3 weeks between cycles. Thus, the maximum number of courses a patient may receive is 10. Response will be evaluated at 7 to 10 days and again just prior to the next dose.

EXAMPLE 5

Protocol for Treatment of Autoimmune Disorders

Patients with certain forms of autoimmune disease, including subsets of patients with the disease aplastic anemia, have increased number of circulating and marrow Tac-positive T cells. In this group of patients, the Tac-positive but not the Tac-negative T cells inhibit hematopoiesis when cocultured with normal bone marrow cells. Patients with elevated number of Tac-positive T cells and associated aplastic anemia receive unmodified anti-Tac monoclonal antibody in 100 ml normal saline with 5% albumin by intravenous administration over a 2 hour period. Patients are treated with 20 mg of anti-Tac three times over a 7 to 10 day period. This course may be modified and repeated if Tac positive cells remain elevated.

An alternative therapeutic approach with anti-Tac is the use of *Pseudomonas* exotoxin anti-Tac according to protocols described above. Patients receive about 200 µg of PE-anti-Tac twice a week during the first week of treatment and at doses of about 2 mg twice a week during the second week.

EXAMPLE 6

Protocol for Treatment to Prevent Allograft Relection

After renal or cardiac allografts and during graft-versus-host disease, certain host T lymphocytes recognize the foreign histocompatibility antigens expressed on the donor organs and thus become activated and express the Tac antigen. Such Tac-expressing activated T cells participate in the rejection of the allografts and in the graft-versus-host disease. The survival of renal allografts was prolonged in cynomolgus monkey recipients treated with the anti-Tac monoclonal antibody.

In patient studies, intravenously administered anti-Tac is added to conventional immunosuppression to prevent allograft rejection. The patients receive anti-Tac monoclonal antibody by intravenous administration in 100 ml of glucose or saline with 5% albumin carrier over about 2 hours. The patients are treated with about 20 mg of anti-Tac daily for about 10 days between the first and tenth day after their receipt of the organ allograft.

Eight patients receiving renal allografts have been treated with the above protocol of anti-Tac in addition to conventional immunosuppression. None of these patients manifested toxicity due to the anti-Tac monoclonal antibody. Furthermore, none of them have rejected the transplanted kidney.

EXAMPLE 7

Therapy of ATL with Anti-Tac Conjugated with Radionuclides

Anti-Tac has been successfully conjugated to the α-particle-emitting radionuclide bismuth-212 and to the β-emitting yttrium-90 by use of bifunctional ligands, such as isobutylcarboxycarbonic anhydride of diethylenetriamine-pentacetic acid (DTPA) or 2-(Pisothiocyantobenzyl)-trans-cyclohexyldiethylenetriamine penta-acetic acid (CHX-A). The physical properties of $^{212}$Bi are appropriate for radio-immunotherapy in that it has a short half-life, deposits its high energy over a short distance, and can be obtained in large quantities from a radium generator. The labeling protocols have been described by Gansow et al. (*Am. Chem. Soc. Symp. Ser.* 241:215–227) and Brechbiel, et al. (1992 *J. Chem Soc Perkin.Trans. I*, 1:1173). DTPA or CHX-A is linked to anti-Tac with $^{14}$C— labeled DTPA used to identify chelate-antibody ratio. DPA (0.2 mM) was dissolved in 2 ml of $H_2O$ by addition of triethylamine (1.38 mM) and lyophilized. The solid formed is taken up in 1 ml of acetonitrile at 4° C. and treated with isobutylchloroformate (0.27 mM) for about 30 minutes, centrifuges, and a 20-µl aliquot of isobutylcarboxycarbonic anhydride solution is reacted with anti-Tac at 4° C. for about 1.5 hours. Sequential dialyses in metal-free buffer are used to purify the protein. A comparable procedure is used to couple anti-Tac to the β-emitting radionuclide yttrium-90. Conjugates with other a or βemitting nuclides are similarly prepared and used. The examples provided herein being only exemplary.

Activity levels of 0.5 µCi or the equivalent of 12 rad/ml of a irradiation targeted by $^{212}$Bi-anti-Tac eliminated more than 98% of the proliferative capacity of the HUT102-B2 cells with only minimal effect on IL-2 receptor-negative lines. This specific cytotoxicity was blocked by excess unlabeled anti-Tac but not by human IgG. Thus, $^{212}$Bi-anti-Tac is an effective and specific immunocytotoxic agent for the elimination of IL-2 receptor-positive ATL cells.

EXAMPLE 8

Clinical Trial of ATL Patients Using $^{90}$Y-Anti-Tac

Eighteen patients with histologically confirmed HTLV-I-associated ATL were studied (Table 1). Each of the patients manifested the following features: (1) a histologically confirmed diagnosis of leukemia or lymphoma of mature T cells with polymorphic indented or lobulated nuclei; (2) expression of the Tac antigen (IL-2Rα) on at least 10 percent of their peripheral blood, lymph node, or dermal T cells, (3) antibodies to HTLV-I demonstrable in the serum; and (4) no cytotoxic chemotherapy and radiation therapy during the 4 weeks before entering into the trial. Patients with or without previous chemotherapy were eligible for inclusion in this study, 10 patients had received previous chemotherapy (Table 2). Patients with symptomatic central nervous system disease were excluded; however, patients with malignant cells demonstrable in the cerebrospinal fluid were included and received intrathecal cytosine arabinoside and/or methotrexate. Patients were required to have a white blood cell count of at least 3,000/mm³, a platelet count of 75,000/mm³, and a life expectancy of at least 1 month. In addition, patients manifesting circulating human antimouse antibodies ("HAMA") were excluded. All patients fulfilling the entry criteria were included in the study. The patients ranged in age from 23 to 63 years (mean 43 years). Five patients were male and 13 female, 16 were black, 1 was Hispanic, and 1 was of Japanese origin. Five were from the United States, five from Jamaica, two from Guyana, two from Trinidad, and one each from Haiti, Grenada, St. Vincent, and Japan. Using the criteria of the Japanese Lymphoma Study Group (Shimoyama, et al. 1991 Br. *J. Haemotol.* 79:428), 11 of the patients with ATL were in the acute stage, 2 manifested ATL lymphoma, and 5 had chronic ATL.

Assay for antibodies to HTLV-I. The sera of ATL patients were analyzed for antibodies to disrupted and inactivated HTLV-I using an enzyme-linked immunosorbent assay (ELISA) (Cellular Products, Buffalo, N.Y.) as previously described (Rubin, et al. *Ann. Intern. Med.*, 113:619).

Figure 4:
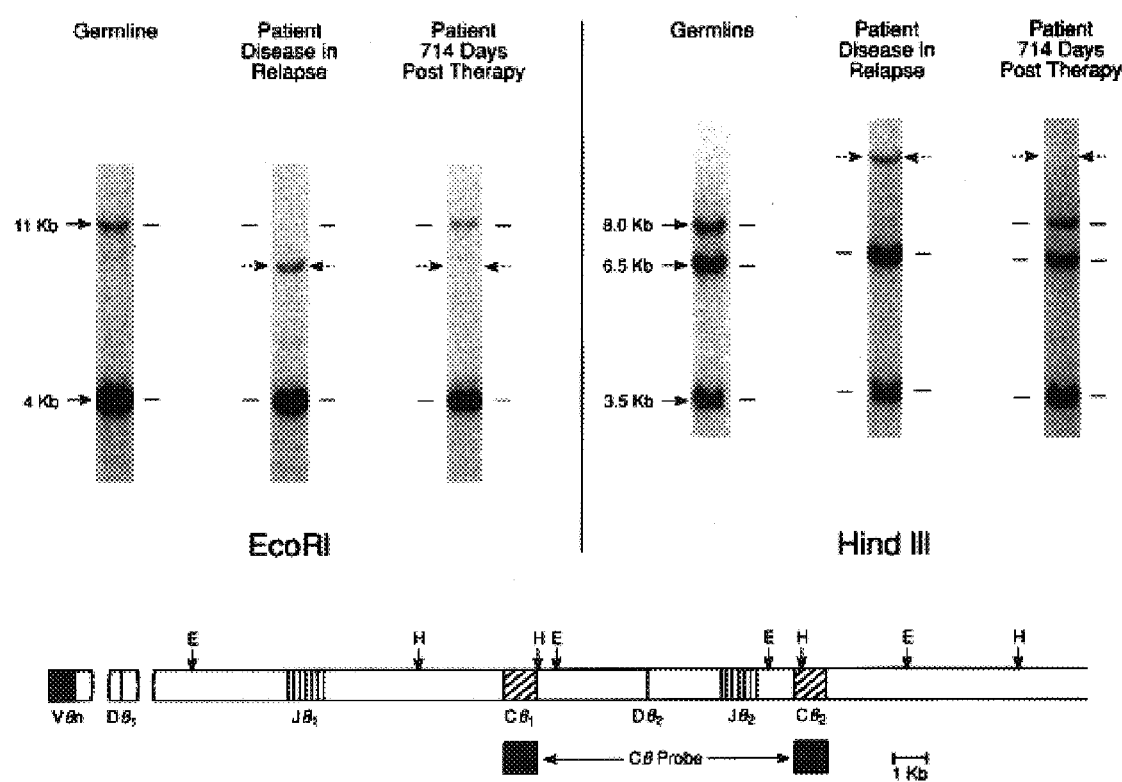
FIG. 4. Analysis of Tcrβ gene rearrangements to monitor $^{90}$Y anti-Tac monoclonal antibody treatment of Patient 7 with ATL using a Tcrβ constant region probe (Cβ). The Tcrβ constant region genes are on 4- and 11-Kb EcORI fragments and on 3.5-, 6.5-, and 8.0-Kb HindIII fragments in germline DNA as indicated (-). The digest of patient peripheral blood DNA during an active phase of the disease prior to the initiation of therapy yielded a diminished 11-Kb EcORI band as well as one nongermline and (→) that identified a monoclonal pattern of Tcrβ gene arrangement. Furthermore, there was a diminution of the 8.0-Kb HindIII digest that reflects a monoclonal Tcrβ pattern of gene rearrangement as well. This Southern blot pattern indicates that one Tcrβ allele in the leukemic clone rearranged to Cβ1, whereas the other allele rearranged to Cβ2. Digests of patient DNA obtained in remission following $^{90}$Y anti-Tac therapy did not reveal the two non-germline brands, thus confirming the elimination of the circulating monoclonal leukemic cell population. In the schematic diagram of the germline arrangement of the Tcrβ gene, we indicate the locations of the EcORI (E) and HindIII (H) restriction endonuclease sites as well as the Cβ regions recognized by the cDNA probe used.

Eighteen patients with histologically confirmed HTLV-I-associated ATL were treated with i.v.-administered $^{90}$Y anti-Tac (Table 1, 2). Two patients had lymphoma-type ATL with normal numbers of peripheral lymphocytes. The peripheral blood white blood cell count before therapy in the remaining 16 patients who had leukemia ranged from 6,400 to 112,800/µl (6.4–112.8×10⁹/L) geometric mean, 18,977×/÷1.22 µl). Patients with ATL had pretherapy serum IL-2R (sIL-2Rα) levels of 2,097 to 102,266 U/ml (2.07–102.266×10⁶U/L) (geometric mean, 12,940×/÷1.41 U/ml), whereas the upper limit of normal is 502 U/ml (mean, 238 U/ml). T-cell leukemic populations were confirmed to be monoclonal by molecular genetic analysis of the genes encoding the T-cell receptor and HTLV-I. Specifically, Southern blot analysis using a radiolabeled probe that hybridizes with the constant region of Tcrβ chain demonstrated a non-germline band indicating a clonal Tcr gene rearrangement, a feature that is the hallmark of a clonally expanded population of T lymphocytes (FIG. 4). Furthermore, Southern blot analysis of HTLV-I proviral integration in Pst-I and EcORI digests of DNA obtained from the circulating mononuclear cells of the patients demonstrated clonal integration of HTLV-provirus (FIG. 5). Clinically, 10 patients manifested involvement of the skin. Eight were hypercalcemic, with a serum calcium level in these cases ranging from 2.54 to 4.50 mmol/L (normal range, 2.05 to 2.50 mmol/L).

Using flow cytometric phenotypic analysis of circulating mononuclear cells, we demonstrated that in the 16 cases with leukemia, the predominant mononuclear cells of the patients expressed the Tac antigen (CD25) on a relatively homogeneous cell population manifesting high fluorescence intensity. In 15 of the 16 cases, the abnormal cell population did not react with the CD7 monoclonal antibody that reacts with normal T-cell precursors and with at least 70 percent of normal mature T lymphocytes.

TABLE 1

Demographic and Clinical Features of ATL Patients

| Patient No. | Type of ATL | Age/Sex/Race | sIL-2R (U/mL) | WBC/µl | Circulating IL-2R/Tac-Expressing Lymphocytes/µl | Serum Ca* mM/l |
|---|---|---|---|---|---|---|
| 1 | Chronic | 42/F/B | 4,026 | 14,600 | 7,100 | 2.32 |
| 2 | Acute | 32/F/H | 47,141 | 23,800 | 8,400 | 2.35 |
| 3 | Acute | 24/F/B | 2,750 | 6,400 | 1,100 | 4.50 |
| 4 | Acute | 55/M/B | 57,626 | 20,100 | 11,990 | 3.45 |
| 5 | Acute | 34/F/B | 2,950 | 11,200 | 5,255 | 2.55 |
| 6 | Chronic | 44/M/B | 2,113 | 6,900 | 2,105 | 2.60 |
| 7 | Chronic | 38/F/B | 2,938 | 32,600 | 27,875 | 2.43 |
| 8 | Chronic | 61/F/B | 7,596 | 37,200 | 32,100 | 2.30 |
| 9 | Acute | 54/F/B | 2,097 | 6,500 | 1,640 | 2.40 |
| 10 | Acute | 48/F/B | 57,065 | 13,900 | 780 | 2.03 |
| 11 | Acute | 23/F/B | 34,825 | 35,600 | 14,800 | 3.51 |
| 12 | Acute | 51/M/B | 81,585 | 14,700 | 2,590 | 2.48 |
| 13 | Lymphoma | 45/M/B | 102,266 | 11,100 | 370 | 2.80 |
| 14 | Chronic | 63/M/B | 3,241 | 8,900 | 4,820 | 2.29 |
| 15 | Acute | 52/F/A | 20,755 | 36,200 | 32,280 | 2.29 |
| 16 | Acute | 37/F/B | 40,927 | 39,300 | 32,900 | 2.32 |
| 17 | Acute | 34/F/B | 54,629 | 112,800 | 89,720 | 4.30 |
| 18 | Lymphoma | 38/F/B | 4,727 | 5,800 | 670 | 2.54 |

Abbreviations: B, black; H, Hispanic; A, Asian; F, female; M, male
*Normal range for serum calcium = 2.05–2.5 mmol/L

TABLE 2

Effect of $^{90}$Y-Anti-Tac Therapy

| Patient No. | Previous Therapy | Doses of $^{90}$Y-anti-Tac Administered Total (per cycle) mCl | Maximum Toxicity ≧ Grade 3/First Cycle Manifested | Development of Human Anti-Murine Anti-Tac Antibodies (HAMA) | Clinical Response/ Duration (Days) | Freedom From Progressive Disease (days) |
|---|---|---|---|---|---|---|
| 1 | BAM-M + RT; murine anti-Tac | 45 (5,5,5,5,5,5,5,5,5) | none | + | CR 896 | 1099 |
| 2 | none | 20 (5,5,5,5) | grade 3 neutropenia and thrombocytopenia cycle 4 | + | PR 364 | 404 |
| 3 | ProMACE; DDI/ AZT/suramin/ solumedrol/ doxorubicin/ cyclophosphamide | 5 (5) | grade 3 thrombocytopenia cycle 1 | NE | PD | 4 |

TABLE 2-continued

Effect of $^{90}$Y-Anti-Tac Therapy

| Patient No. | Previous Therapy | Doses of $^{90}$Y-anti-Tac Administered Total (per cycle) mCi | Maximum Toxicity ≧ Grade 3/First Cycle Manifested | Development of Human Anti-Murine Anti-Tac Antibodies (HAMA) | Clinical Response/ Duration (Days) | Freedom From Progressive Disease (days) |
|---|---|---|---|---|---|---|
| 4 | murine anti-Tac none | 20 (10,5,5) | grade 4 neutropenia cycle 1 grade 3 thrombocytopenia cycle 1 grade 3 hepatotoxicity cycle 1 grade 3 cardiac toxicity cycle 1* | + | PR 307 | 399 |
| 5 | CHOP; COP | 45 (10,10,10,10,5) | grade 3 thrombocytopenia cycle 4 | – | PR 215 | 263 |
| 6 | CHOP | 66 (10,10,10,6,10,10,10) | grade 3 neutropenia cycle 5 | + | Unevaluable | 1353+ |
| 7 | none | 50 (15,15,10,5,5) | grade 4 neutropenia and thrombocytopenia cycle 3 grade 3 hepatotoxicity cycle 2 | – | PR 91, CR 1013+ | 1049+ |
| 8 | CHOP | 20 (15,5) | grade 4 neutropenia and grade 3 thrombocytopenia cycle 1 | – | stable disease | 138 |
| 9 | ProMACE-CytaBOM | 25 (15,10) | grade 3 neutropenia cycle 2 | – | PR 178 | 186 |
| 10 | none | 15 (10,5) | grade 4 neutropenia cycle 1 grade 3 hepatotoxicity cycle 1 grade 3 thrombocytopenia cycle 2 | – | PD | 43 |
| 11 | ProMACE-CytaBOM | 10 (10) | none | – | PD | 26 |
| 12 | ProMACE-CytaBOM; cisplatin/ cytarabin/ dexamethasone | 10 (10) | none | NE | Died before response could be determined | 23 |
| 13 | CHOP, ProMACE-CytaBOM | 10 (10) | grade 4 thrombocytopenia cycle 1 | – | PD | 28 |
| 14 | none | 10 (10) | none | + | PR 681 | 708 |
| 15 | none | 15 (10,5) | grade 4 neutropenia cycle 1 | + | PR 49 | 77 |
| 16 | none | 20 (10,10) | grade 3 renal toxicity cycle 2 | – | PD (mixed response) | 49 |
| 17 | none | 35 (10,5,5,5,5,5) | grade 4 thrombocytopenia cycle 6 grade 4 neutropenia cycle 6 | – | PR 400 | 405 |
| 18 | CHOP | 10 (10) | none | NE | PD | 26 |

Abbreviations: ProMACE-CytaBOM, prednisone, methotrexate, doxorubicin, cyclophosphamide, etoposide, cytosine arabinoside, bleomycin, vincristine, Leucovorin; BAM-M, bleomycin, adriamycin methotrexate and topical nitrogen mustard; CHOP, cyclophosphamide, doxorubicin, vincristine, prednisone; COP, cyclophosphamide, vincristine, prednisone; RT, radiotherapy; DDI, didanosine; AZT, zidovudine; CR, complete remission; PR, partial response; SD, stable disease; PD, progressive disease; NE, not evaluated.
*The cardiac toxicity in this patient was orthopnea that occurred while he was receiving large fluid volume to control hypercalcemia. It quickly resolved with Furosemide therapy and did not recur.

EXAMPLE 9

Production of the anti-Tac monoclonal antibody. The anti-Tac monoclonal antibody, a mouse IgG2a monoclonal anybody, was produced as described previously (Waldmann, et al. 1993 *Blood,* 82:1701). The lots used were greater than 99 percent pure IgG as assessed by high-performance liquid chromatography and sodium dodecylsulfate-polyacrylamide gel electrophoresis.

Studies with $^{111}$In-labeled anti-Tac to monitor of sIL-2Rα on delivery of radiolabeled anti-Tac to tumor cells. Prior to the initiation of the therapeutic 90Y anti-Tac trial, $^{111}$In-labeled anti-Tac monoclonal antibody was administered to five patients to define the pharmacokinetics of radiolabeled anti-Tac, to perform dosimetry calculations, and to monitor the impact of circulating sIL-2Rα on our ability to deliver radionuclide-labeled anti-Tac to tumor cell targets. In the initial studies, $^{111}$In-labeled anti-Tac was administered to five patients in association with a total anti-Tac antibody dose of 1 mg (radiolabeled and unlabeled). One week later, the same dose of radioindium-labeled anti-Tac was administered to the same patients in association with a total dose of 50 mg of the anti-Tac monoclonal antibody. When a low total quantity (1 mg of total antibody) of radiolabeled anti-Tac was administered, high levels of circulating antigen (sIL-2R) were shown to interfere with tumor cell targeting by binding to the administered antibody, thus reducing antibody access to cellular targets. Soluble IL2Rα expression had a major effect on the bioavailability of infused anti-Tac. For example, when 1 mg of radiolabeled antibody was administered to patients with high IL-2R levels (e.g. 230,370 U/ml), virtually no radioindium bound to circulating leukemic cells, there was only minimal anti-Tac binding to these circulating Tac-expressing cells demonstrable by flow cytometry, and there was poor targeting of radioindium to tumor-bearing lymph nodes as assessed by gamma camera scan imaging.

To define the bindability of circulating radioindium-labeled anti-Tac, we used a quantitative assay to determine the bioactivity ex vivo infused antibodies as a function of circulating IL-2R levels. In these studies, the radiolabeled $^{111}$In anti-Tac circulating in the patient's serum was assessed ex vivo for its capacity to bind to the IL-2R-expressing T-cell line HUT 102 over the 30 minutes of incubation at 4° C. When a small quantity such as the 1 mg/patient dose of high specific activity 9Y anti-Tac was administered to patients with high sIL-2R levels, only a small fraction of the anti-Tac in the circulation remained unblocked by bound sIL-2R and was therefore able to bind to the HUT 102 cells ex vivo. The bioavailable fraction of the indium-labeled anti-Tac increased markedly when the quantity of anti-Tac administered in association with the radiolabeled antibody was increased from 1 mg to 50 mg/patient. We extended these observations by administering $^{111}$In anti-Tac to 16 of the patients receiving anti-Tac as part of the yttrium-90 therapeutic protocols and demonstrated that a linear relationship exists between sIL-2Rα concentration and the amount of antibody required to achieve different fractions of circulating bioavailable antibody. In the Phase I trial discussed below, we administered a total dose of 10 mg of anti-Tac to all patients. However, based on the bioavailability data obtained during this initial phase of the study, in the Phase II trial we administered a quantity of anti-Tac (2,5, or 10 mg) at each infusion that was chosen on the basis of the patient's soluble sIL-2R concentration determined within 3 weeks of the infusion.

EXAMPLE 10

Chelation and radiolabeling of anti-Tac. The anti-Tac preparation was conjugated to the 2-(4-isothiocyanatobenzyl)-6-methyl-diethylenetriamine pentaacetic acid (lB4M-DTPA) or 2-(P-isothiocyantobenzyl) trans-cyclohexyl-diethylenetriamine penta-acetic acid (CHX-A) using the procedures of Brechbiel and Mirzadeh et al (Brechbiel, et al. 1991 *Bioconjugate Chem.*, 2:187; Merzadeh, et al. 1990 *Bioconjugate Chem.*, 1:59). Radiolabeling was performed using $^{90}$Y for therapy and satin for imaging. In brief, approximately 1 mg of conjugated anti-Tac was put into a propylene vial that served as the reaction vessel and allowed to react with $^{90}$Y or $^{111}$In. Excess DTPA was then added to complex unreacted ionic metal isotope and the anti-Tac bound fraction was purified by preparative size exclusion HPLC using (TSK 3000). The radioactivity in the final product was over 98 percent protein bound as determined by instant thin layer chromatography using plastic-backed silica gel plates (10 percent ammonium fomate/methanol/citric acid 0.2M). This radiochemical purity was confirmed by analytical HPLC. All products passed sterility and pyrogen testing. Labeled antibody was injected within 24 hours of labeling.

EXAMPLE 11

Therapeutic study plan. All patients were hospitalized and received the anti-Tad monoclonal antibody labeled with $^{90}$Y intravenously over a 2-hour period. Nine patients with ATL were initially treated in a Phase I dose escalation trial. In this Phase I trial, groups of three patients were scheduled to receive escalating doses of 90Y anti-Tac, which started at 5 mCi and then in subsequent groups of patients increased by 5 mCi increments until a maximum tolerated dose not requiring support by bone marrow transplantation was determined. Three patients each received 5, 10, and 15 mCi $^{90}$Y anti-Tac. Nine additional patients received 10 mCi 90Y anti-Tac in a Phase II trial. The entry criteria were identical for the Phase I and Phase II trials. Patients that manifested a partial or complete remission were eligible to receive up to eight additional cycles of treatment (with at least 6-week intervals between cycles) provided that they did not develop circulating HAMA. Retreatment was delayed until the blood counts returned to the range that was originally required for entry. Retreatment with 90Y anti-Tac was at the same dose as the initial therapy for those patients that did not develop grade ≧3 hematopoietic toxicity following the previous dose, whereas it was reduced to 10 or 5 mCi (Table 2) for individuals who had developed grade 3 or greater toxicity following therapy. Unlabeled unconjugated anti-Tac was mixed with the radiolabeled anti-Tac to control the total quantity (in mg) of antibody administered. The nine patients in the initial Phase I study received 10 mg of anti-Tac per infusion.

EXAMPLE 12

Bioavailability, dosimetry, and imaging studies. Prior to the initiation of the 9Y anti-Tac therapeutic trial, $^{111}$In-labeled anti-Tac monoclonal antibody was administered to five patients with ATL on two occasions in association with total doses of 1 and 50 mg of anti-Tac, respectively, in order to define the in vivo pharmacokinetics of radiolabeled anti-Tac and to perform dosimetry calculations. Furthermore, these studies were used to determine the optimal quantity of anti-Tac to administer to the ATL patients who manifest sIL-2Rα antigenemia in order to deliver the highest fraction of the infused radiolabeled antibody to the tumor cells. In addition, $^{111}$In-labeled anti-Tac was infused on up to three occasions per patient in association with $^{90}$Y anti-Tac administration in the Phase I and II therapeutic trials. Since soluble IL-2Rα is present in the circulation, the bioavailability of $^{111}$In anti-Tac in ex vivo plasma was determined prior to and at various times following infusion. In these studies, the radiolabeled $^{111}$In anti-Tac circulating in the patient's serum was assessed immediately ex vivo for its capacity to bind to the IL-2R-expressing T-cell line HUT-102. In addition, gamma camera scans were performed using the $^{111}$In anti-Tac at the initiation of the therapeutic trials and during subsequent cycles. These scans were interpreted by a single experienced reader and were compared with prestudy physical examination and with other appropriate radiographic studies. Furthermore, scans performed during courses at retreatment were compared to those obtained during the first therapeutic cycle.

Computer-assisted analysis of images obtained from patients receiving $^{111}$In monoclonal antibody, scintigraphic data, and serial pharmacokinetic estimates were used in the dosimetry for $^{90}$Y-labeled anti-Tac. A 10-mCi dose of $^{90}$Y anti-Tac administered to a patient was calculated to yield radiation of approximately 148 cGy to the marrow, 228 cGy to the liver, and 336 cGy to the spleen. The calculated radiation dose to the tumor represents a range of doses across a population of patients who target $^{90}$Y radiolabeled antibody to varying extents. The estimated dose to the tumor with the 10-mCi dose ranged from 302 to 908 cGy.

EXAMPLE 13

Evaluation of toxicity. Toxicity was evaluated according to the National Cancer Institute's Common Toxicity Criteria. Complete blood cell and platelet counts were obtained prior to each infusion, at 24 and 48 hours, as well as 6 to 10 days and 4 to 6 six weeks following each infusion. Hepatic enzyme, renal and electrolyte studies, and urine analysis were performed at 24 hours and weekly during the Phase I study and at 4 to 6 weeks during Phase II.

The serum was assayed for soluble IL-RA by an ELISA technique described previously (Rubin, et al. 1990 *Ann. Intern. Med.*, 113:619). Furthermore, the serum was assayed for human antimurine anti-Tac levels for a given patient were considered meaningfully increased with the antibody level after therapy was on the linear part of the curve and was greater than 250 ng/ml.

Toxicity. Eighteen patients with ATL were treated with $^{90}$Y-labeled anti-Tac. Three patients each were studied at 5, 10, and 15 mCi doses. The remaining nine patients were studied subsequently in a Phase II trial involving an initial dose of 10 mCi of $^{90}$Y-labeled anti-Tac per dose. Patients undergoing a partial or complete remission were permitted to receive up to eight additional doses of $^{90}$Y-labeled anti-Tac. The mean number of dose cycles was 3 (range 1–9). The 18 patients received a total of 55 distinct cycles of therapy with an aggregate dose for individual patients ranging from 5–66 mCi over the total treatment course (mean, 23 mCi/patient).

The predominant toxicity observed in the ATL patients following $^{90}$Y anti-Tac administration was hematologic depression (Table 2). However, grade 3 transient hepatic toxicity occurred in 3 of the 54 evaluable treatment cycles and four patients developed transient proteinuria. There were three early adverse events observed in the 18 patients under study. One patient died of unexplained cardiac asystole 23 days following administration of $^{90}$ anti-Tac. This patient, who did not manifest hematologic toxicity, was an individual with end-stage glaucoma, hypertension, diabetes, and hypercalcemia prior to therapy. One patient died of progressive disease 10 days following therapy. One patient manifested very early neutropenia that was believed to be related to other drugs, including allopurinol. This neutropenia resolved when the other medications were discontinued. No recurrence of this early hematopoietic toxicity was observed when the patient was retreated with $^{90}$Y anti-Tac.

The most common pattern of toxicity observed in the patients was thrombocytopenia and granulocytopenia appearing initially at 4 to 5 weeks following $^{90}$Y anti-Tac therapy with nadir values usually occurring during weeks 5 to 7 following treatment. Focusing on this pattern of toxicity, following the first administration of 90Y anti-Tac, one of three patients receiving 5 mCi of $^{90}$Y anti-Tac developed grade 3 hematopoietic toxicity. Three of the 12 patients receiving 10 mCi of $^{90}$Y anti-Tac developed grade 3 or 4 thrombocytopenia or granulocytopenia during weeks 5 to 8 following the initial course of therapy and received a reduced dose in subsequent courses of therapy. Of the 3 patients receiving 15 mCi of 9 anti-Tac, one developed grade 4 hematopoietic toxicity, whereas, the remaining two did not manifest this grade of hematopoietic toxicity following the first administration of $^{90}$ anti-Tac. Cumulative toxicity was observed in patients who received multiple doses of $^{90}$Y anti-Tac. Focusing on the three patients receiving an initial dose of 5 mCi $^{90}$Y anti-Tac, one never developed grade 3 or grade 4 granulocytopenia over nine courses of therapy, whereas the others developed grade 3 hematopoietic toxicity following the first or fourth cycles of therapy. Three patients who did not manifest grade 3 or 4 toxicity after an initial dose of 10 mCi received additional doses. Two of three patients developed grade 3 or 4 hematocytopenia for the first time following the fourth or fifth cycles of therapy.

A single patient manifested a late toxic event, the development of a myelodysplastic syndrome and Sweet's Syndrome that progressed to myelogenous leukemia and death approximately 3 years following the initial induction of a complete remission. The patient had received 3 months of BAM-M (bleomycin adriamycin, methotrexate, and topical nitrogen mustard) chemotherapy, 30 Gy of external beam irradiation to the lumbar spine as well as courses of unmodified murine anti-Tac prior to entry into the anti-Tac trial.

EXAMPLE 14

Tumor response. Tumor response was assessed by physical examination and CAT scan. In addition, pretreatment and posttreatment $^{111}$In anti-Tac imaging studies evaluated for follow-up of lymph node, spleen, and skin involvement. Furthermore, the number of circulating cells expressing leukemic cell phenotype was monitored by direct and indirect immunocytofluoroscopy using a fluorescence-activated cell sorter as discussed previously (Waldmann, et al. 1993 *Blood* 82:1701). Two antibodies (anti-Tac and 7G7/B6) that are directed toward different epitopes of IL-2Rα were used to identify the expression of this receptor subunit. Other monoclonal antibodies used included antibodies that react with human T-cell associated antigens [(CD2, CD3, CD4, and CD8; Ortho and Becton-Dickinson, Mountain View, Calif.); CD7 (3A1; a gift from Dr. Barton Haynes)]. Fluorescein isothiocyanate (FITC)-labeled goat anitmouse IgG and IgM reagent was obtained from Cal Tag (San Francisco, Calif.). The absolute number of cells in the circulation per cubic millimeter expressing a particular antigen was determined from the product of (1) circulating white blood cell count per cubic millimeter, (2) the proportion of circulating while blood cells that were mononuclear cells as determined by routine hematologic analysis, and (3) the proportion of these mononuclear cells that expresses the antigen under study as assessed by immunocytofluoroscopy.

In addition, molecular genetic analysis of T-cell antigen receptor (Tcr) gene rearrangements and HTLV-1 integration were performed as described previously. These analyses were performed on peripheral blood mononuclear cells at the initiation of therapy and at subsequent periods to monitor the efficacy of therapy in eliminating the monoclonal T-cell receptor. The restriction enzymes BamHI, EcORI, and HindIII were used in the analysis of T-cell receptor gene rearrangement, whereas EcORI and Pst-I (International Biotechnologies, New Haven, Conn., and New England Biolabs, Beverly, Mass.) were used in the analysis of HTLV-1 integration to distinguish monoclonal from polyclonal integration of this retrovirus.

The criteria for therapeutic response were as follows: (1) complete response, disappearance of all measurable and assessable disease lasting more than 1 month; (2) partial response at least, a 50 percent reduction of leukemic cell count, a 50 percent reduction in the size of all measurable lesions-, and no new lesion for 1 month; (3) stable disease, less than a partial response with no new lesion or less than a 25 percent increase in leukemic cell count or an increase of 25 percent or greater in any measurable lesion.

Sixteen of the 18 patients with histologically confirmed ATL had measurable disease and survived for at least 3 weeks following therapy and were thus evaluable for their therapeutic response (Table 2). Seven of these 16 patients had either a transient response (less than 1 month), a mixed response with a 50–95 percent reduction in the number of circulating leukemic cells but an increase in the size of lymph nodes, or developed progressive disease following their initial $^{90}$Y anti-Tac at a period when they were experiencing progressive disease despite the fact that they had been receiving multi-agent chemotherapy up to 1 to 2 months prior to starting on the $^{90}$Y anti-Tac protocol. The remaining nine patients had a more favorable to therapy. Seven patients, one with chronic ATL and six with acute ATL, developed a partial remission. The duration of these partial remissions ranged from 49 to 681 days (mean, 280 days). Six patients of this group manifesting partial remissions received subsequent courses of $^{90}$Y anti-Tac until they developed HAMA, persistent hematologic toxicity, or progressive disease.

Figure 8:
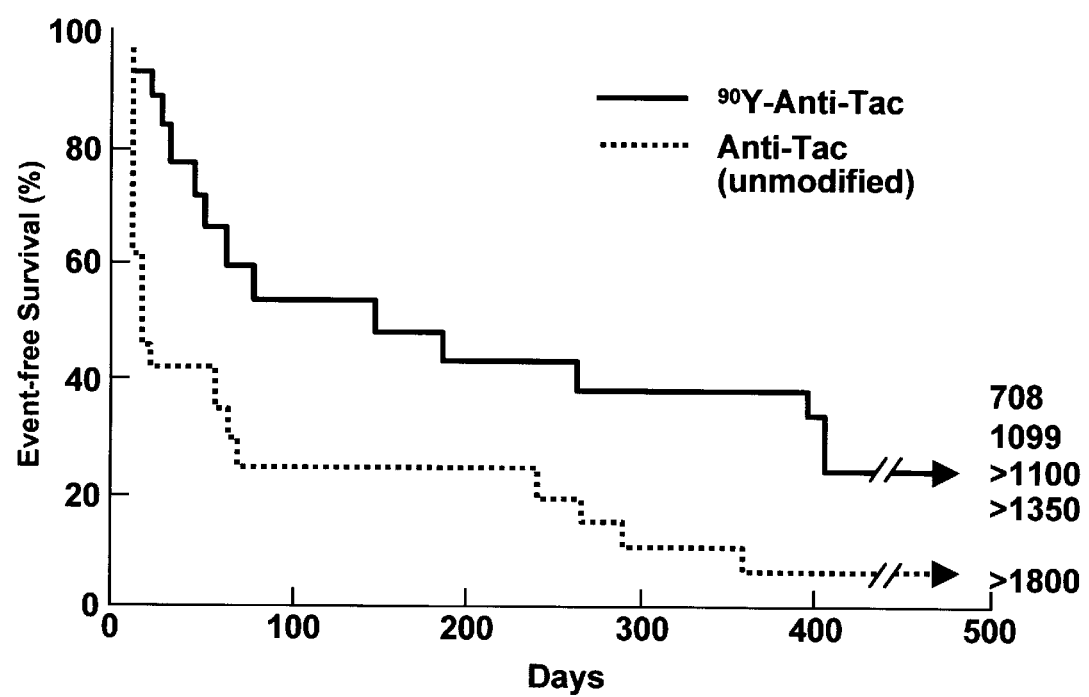
FIG. 8. A Kaplan-Meier plot (1958 *J. Am. Stat. Assoc.* 53:457) of event-free survival (surviving patients without progressive disease) comparing patients treated with unmodified anti-Tac (- - -) with those receiving $^{90}$Y anti-Tac (-).

Two additional patients developed complete remission. One of these patients developed a myelodysplastic picture progressing to myelogenous leukemia that terminated in her death 1,099 days following initiation of therapy. Although the cause of death in this case was the secondary myelogenous leukemia, cells with ATL morphology were detected in the skin at autopsy examination. The remaining patient continues in complete remission more than 3 years following therapy initiation. The observations that support these conclusions concerning the favorable therapeutic responses include the demonstration of a reduction in size of all measurable lesions as assessed by physical examination, CAT scan (FIG. 6), and gamma camera imaging studies following intravenous co-administration of $^{111}$In anti-Tac (FIGS. 6,8). Furthermore, the clinical responses in all patients with leukemia were associated with a reduction in the number of peripheral blood leukemic cells enumerated by FACS analysis (FIG. 7A), by a decline in the sIL-2R concentration (FIG. 7B), and a normalization of the Southern blot patterns of Tcrβ gene arrangement and HTLV-I integration (FIG. 5). Normal T cells can be distinguished from leukemic cells in the patients by FACS analysis in that the normal cells express the CD7 antigen, whereas the leukemic cells of most patients do not. In patients manifesting a partial or complete remission, the CD25$^+$CD7$^-$ leukemic cells were reduced in the number or were absent, whereas the CD7$^+$ expressing CD 25$^-$ nonexpressing normal T cells persisted at near pre-therapy levels (FIG. 7A), indicating good Tac-expressing tumor cell specificity of the therapeutic response.

Among the nine patients with a partial or complete remission following $^{90}$Y anti-Tac therapy, three had received previous chemotherapy, three manifested hypercalcemia, and three had liver function abnormalities prior to $^{90}$Y anti-Tac therapy. During the period of partial or complete remission there was a normalization of the serum calcium level in each case. Furthermore, liver function tests normalized or improved following therapy in each of the three patients that manifested liver function abnormalities before therapy.

The routine hematologic and immunofluorescence analyses discussed above usually yield valid conclusions concerning the efficacy of monoclonal antibody therapy. However, care must be taken when interpreting immunofluorescence analyses because a monoclonal antibody could theoretically cause modulation of its target antigen from the cell surface without leading to cell death. Furthermore, antibody therapy might select for the expansion of a variant leukemic cell subpopulation that does not express the antigen targeted by the antibody. To address this concern, the observed clinical remissions were confirmed by molecular genetic analysis of the arrangement of the gene encoding the beta chain of the Tcr. In particular, the two complete clinical remissions were confirmed by molecular analysis of the Tcrβ gene arrangement by demonstrating that the novel nongermline band on Southern analysis of peripheral blood mononuclear cell that was characteristic of a monoclonal expansion of T-cell observed pre-therapy was no longer demonstrable following therapy (FIG. 4). Furthermore, the complete remissions in these two patients were confirmed by molecular genetic analysis of integrated HLTV-1 provirus in the circulating mononuclear cells (FIG. 5). Before therapy the patients manifested a monoclonal HTLV-1 integration pattern on EcORI and Pst-I digests of their mononuclear cell DNA. The band(s) on Southern analysis that had established the monoclonal HTLV-I integration pre-therapy were decreased in intensity in each of the five patients undergoing a partial remission who were reevaluated during this period and were no longer demonstrable in the cells of the two patients who were evaluated when they were in a complete remission.

EXAMPLE 15

Immunologic competence and production of a human anti-mouse antibody (HAMA) response to the infused monoclonal antibody. One of the major clinical features associated with ATL is a profound immunodeficiency state affecting both cellular and humoral immunity. Before therapy only 4 of the 18 patients manifested a positive skin test response to one or more of the seven recall skin test antigens assessed by the Merieux multi-test skin test procedure. Furthermore, only one of the patients manifested HAMA within the 8 weeks following initiation of anti-Tac therapy. None of the seven patients failing anti-Tac therapy developed a positive skin test response to recall antigens following therapy or made a HAMA response to the infused mouse monoclonal antibody.

Eight patients who were anergic prior to therapy manifested a partial or complete remission following anti-Tac therapy. Five of these eight initially anergic patients developed a delayed hypersensitivity response to one or more of the seven recall skin test antigens during remission. Furthermore, five of the nine patients who underwent a partial or complete clinical remission, as well as one patient without evaluable disease, initially developed HAMA to the infused anti-Tac following the first, second, third (two cases), seventh, or ninth course of $^{90}$Y murine anti-Tac administration. This development of HAMA precluded further administration of $^{90}$Y anti-Tac. Thus, effective IL-2R-directed therapy of patients with ATL is associated in some cases with a return of cellular and humoral immune functions.

EXAMPLE 16

Consenting patients receive an initial dose of 10 mCi of $^{90}$Y-anti-Tac. Up to 5 mCi of $^{111}$In-anti-Tac on up to three occasions are infused simultaneously with $^{90}$Y anti-Tac to allow visualization by scans. The radiolabeled antibodies are diluted appropriately in a normal saline 5% human serum albumin solution and administered intravenously with a slow infusion (2 hr.). Vital signs are monitored closely during each therapeutic administration (hourly for the first 4 hr. every 2 hr for the next 8 hr, and then per routine), and emergency support for anaphylactic reactions is available. All patients receive their infusion as inpatients, and if they are not local residents, they remain as an inpatient for the subsequent 7 days.

Thirty patients with CTCL and 30 patients with PTCL are treated at the 10-mCi dose level of $^{90}$Y. Patients receive only one infusion every 6 weeks. Up to 5 mCi of $^{111}$In-anti-Tac is administered to certain patients on up to 3 occasions simultaneously to follow the kinetics of disappearance of anti-Tac from the plasma, to define the distribution of radiolabeled anti-Tac, and to allow visualization by scans. The quantity of anti-Tac administered at each infusion to patients with CTCL and PTCL is determined by their soluble serum IL-2R levels. Patients with soluble IL-2R of under 2,000 units/ml receive 2 mg of humanized anti-Tac, those with 2,000 to 10,000 units/ml receive 5 mg of humanized with Tac, those with 10,000 to 50,000 units/ml, receive 10 mg of humanized anti-Tac, and those with soluble IL-2R of more than 50,000 receive 20 mg. For patients receiving cycles of retreatment, the dose of humanized anti-Tac administered (i.e., 2, 5, 10, 20 mg) may be adjusted on the basis of the estimate of the serum soluble IL-2R level obtained within 3 weeks prior to the dose administration. The levels of anti-Tac are those estimated to yield binding of radiolabeled anti-Tac to all circulating Tac-expressing tumor cells and to produce approximately 25 to 75% saturation of the IL-2 receptors. These calculations are made on the basis of the observations during the Phase I trial, where binding was assessed by FACS analysis and by binding to the circulating cells of $^{111}$In-anti-Tac to co-administered with $^{90}$Y-anti-Tac.

Patients without evidence of progression may be eligible to receive up to 6 further infusions of $^{90}$Y-humanized anti-Tac at a dose of 5 mCi with at least 6 weeks between treatments and with at least a 2–3 day interval following cessation of G-CSF administration. Thus, the maximum number of courses a patient might receive is 7. Response is evaluated at 7 to 10 days and again during the period 4 to 6 weeks following administration of $^{90}$Y-humanized anti-Tac. Patients who have circulating antibodies to the infused humanized anti-Tac antibody (sensitivity of assay 250 ng/ml) is not eligible for further infusions.

G-CSF is administered subcutaneously at a dose of 5 µg/kg daily to patients whose neutrophil count falls below 1,000/mm$^3$. The G-CSF may be continued for up to 45 days or until the neutrophil count exceeds 10,000/mm$^3$. Patients are instructed regarding the self-administration of G-CSF prior to discharge from the hospital. G-CSF administration must be terminated 2–3 days prior to a retreatment dose of $^{90}$Y-anti-Tac. G-CSF will be obtained from the Clinical Center Pharmacy.

EXAMPLE 17

Rationale for Yttrium-90-($^{90}$Y)—Humanized Anti-Tac Dose Selection

Yttrium-90-humanized anti-Tac is contemplated for use as a therapeutic modality in the treatment of Tac-expressing mature T-cell malignancies other than ATL. An initial radiation dose of 10 mCi 90Y has been selected on the basis of the Phase I trial with Yttrium-90-murine anti-Tac where it was an effective well-tolerated dose and is identical to the dose currently being used for ATL. The higher dose, 15 mCi, in the Phase I trial led to Grade III–IV toxicity that interfered with the ability to administer subsequent $^{90}$Y-anti-Tac doses.

Subsequent doses have been reduced to 5 mCi on the basis of the Phase I/II trial with $^{90}$Y-murine anti-Tac wherein repeated administration of 10 mCi led to progressive hematopoietic toxicity that interfered with the ability to administer subsequent 10 mCi $^{90}$Y-anti-Tac doses. We justify the initial 10-mCi $^{90}$Y-anti-Tac dose based on the following: (a) it is ½ of that known to give Grade III–IV toxicity in clinical trials using 90Y bound to murine antibody with a less effective chelate; (b) it is the dose that gave modest toxicity using the identical chelate linked to murine anti-Tac; (c) absorbed dose calculations for the bone marrow indicated this dose to be in a safe range; (d) it is 10% of the dose/kg that gives Grade III toxicity in rhesus monkeys and (e) is identical to the dose of $^{90}$Y-T101 permitted and identical to the dose of $^{90}$Y humanized anti-Tac permitted in 93-C-0066 for treatment of patients with ATL.

A 10 mCi dose is calculated to give 148 cGy to the marrow, a dose in a range expected to give modest toxicity.

Dose estimates to the liver, spleen, and whole body are derived from averages across 3 patients studied. The liver is expected to receive a dose of 228 cGy (456 cGy assuming 100% error) at the 10-mCi dose level which is within safe limits based on the results in the hepatoma trial. The spleen is expected to receive a large dose of up to 336 cGy at the 10-mCi dose. At this dose, we expect reversible cytoreduction of the spleen.

The calculated radiation dose to tumors represents the range of doses that are expected across a population of patients who target to varying extents. The dose expected to tumor ranges from 302–908 cGy at the 10mCi dose. It may be possible to achieve a therapeutic benefit in these dose ranges based on previous experience with $^{90}$Y-murine anti-Tac and based on classical radiation biological analysis due to the radiation sensitivity of the target T-lymphocyte population.

TABLE 3

Radiation Dose Estimates (in cGy) to Tumor and Critical Organs for Intravenously Administered $^{90}$Y-Anti-Tac

| Compartment | Radiation Dose (cGy) for 10 mCi of $^{90}$Y Anti-Tac |
| --- | --- |
| Tumor* | 302–908 |
| Marrow** | 148 |
| Liver | 228 |
| Spleen | 336 |
| Whole | 18 |

*Based on tumor biopsy data with T101 antibody.
**Based on marrow biopsy with murine anti-Tac monoclonal antibody.

It is understood that the examples and embodiments described herein are for illustrative purposes only and should not be construed as limitations on the scope of the invention. Various modifications or changes in light thereof will be suggested to persons skilled in the art and are to be included within the spirit and purview of this application and scope of the appended claims.

What is claimed is:

1. A method of reducing levels of Tac-positive cells in patients with elevated levels of Tac-positive cells comprising the steps of,
    a) determining a dosage, said dosage comprising 5–15 mCi $^{90}$Y-conjugated anti-Tac in a total amount of 2–20 mg anti-Tac, wherein the dose is 2 mg total anti-Tac if said patient has sIL-2R levels of less than 2,000 units/ml, the dose is 5 mg total anti-Tac if said patient has sIL-2R levels of 2,000–10,000 units/ml, the dose is 10 mg of total anti-Tac if the patient has sIL2R levels of 10,000–50,000 units/ml, and the dose is 20 mg of total anti-Tac if said patient has sIL-2R levels of greater than 50,000 units/ml; and
    b) administering said dosage to said patient to eliminate disease-associated Tac-positive cells.

* * * * *